(12) United States Patent
Weisman et al.

(10) Patent No.: US 11,173,070 B2
(45) Date of Patent: Nov. 16, 2021

(54) HETEROGENEOUS FOAM MATERIALS HAVING A GRAPHIC PRINTED THEREON

(71) Applicant: The Procter & Gamble Company, Cincinnati, OH (US)

(72) Inventors: Paul Thomas Weisman, Cincinnati, OH (US); Hui Yang, Cincinnati, OH (US); Alrick Vincent Warner, Loveland, OH (US); David Christopher Oetjen, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1183 days.

(21) Appl. No.: 15/138,267

(22) Filed: Apr. 26, 2016

(65) Prior Publication Data

US 2016/0317354 A1 Nov. 3, 2016

Related U.S. Application Data

(60) Provisional application No. 62/153,535, filed on Apr. 28, 2015.

(51) Int. Cl.
*B32B 3/10* (2006.01)
*A61F 13/00* (2006.01)
(Continued)

(52) U.S. Cl.
CPC .. *A61F 13/00059* (2013.01); *A61F 13/00017* (2013.01); *A61F 13/00042* (2013.01); *A61F 13/00068* (2013.01); *A61F 13/0223* (2013.01); *A61F 13/51394* (2013.01); *A61F 13/53* (2013.01); *A61F 2013/53081* (2013.01);
(Continued)

(58) Field of Classification Search
None
See application file for complete search history.

(56) References Cited

U.S. PATENT DOCUMENTS 3,929,135 A 12/1975 Thompson
4,324,246 A 4/1982 Mullane et al.
(Continued)

FOREIGN PATENT DOCUMENTS

CN 203468873 U 3/2014
WO WO 2013/180937 12/2013

OTHER PUBLICATIONS

PCT/US2016/029430 PCT International Search Report, dated Aug. 4, 2016, 13 pages.

*Primary Examiner* — Christopher M Polley
(74) *Attorney, Agent, or Firm* — William E. Gallagher

(57) ABSTRACT

The present disclosure relates to homogeneous or heterogeneous polymer foam structures having a graphic printed thereon. As discussed herein, foam structures, such as for example High Internal Phase Emulsion (HIPE) foam structures may include a first surface and a second surface opposite the first surface, and one or more graphics may be printed directly on the first and/or second surfaces of the foam. The graphic may comprise ink positioned on the first and/or second surface, wherein the ink may penetrate into the foam structure below the surface on which the ink is applied. As such, the ink may reside on the foam structure and/or within the foam structure at various depths below the first and/or second surface.

56 Claims, 9 Drawing Sheets

(51) Int. Cl.
*A61F 13/53* (2006.01)
*A61F 13/513* (2006.01)
*A61F 13/02* (2006.01)
*A61F 13/84* (2006.01)

(52) U.S. Cl.
CPC ............. *A61F 2013/530649* (2013.01); *A61F 2013/530817* (2013.01); *A61F 2013/8497* (2013.01)

(56) References Cited

U.S. PATENT DOCUMENTS

| | | |
|---|---|---|
| 4,342,314 A | 8/1982 | Radel et al. |
| 4,463,045 A | 7/1984 | Ahr et al. |
| 4,609,518 A | 9/1986 | Cum et al. |
| 4,629,643 A | 12/1986 | Curro et al. |
| 4,940,464 A | 7/1990 | Van Gompel et al. |
| 4,950,254 A | 8/1990 | Andersen et al. |
| 5,006,394 A | 4/1991 | Baird |
| 5,092,861 A | 3/1992 | Nomura et al. |
| 5,167,897 A | 12/1992 | Weber et al. |
| 5,246,433 A | 9/1993 | Hasse et al. |
| 5,360,420 A | 11/1994 | Cook et al. |
| 5,387,207 A | 2/1995 | Dyer et al. |
| 5,500,451 A | 3/1996 | Goldman et al. |
| 5,569,234 A | 10/1996 | Buell et al. |
| 5,599,335 A | 2/1997 | Goldman et al. |
| 5,628,097 A | 5/1997 | Benson et al. |
| 5,643,588 A | 7/1997 | Roe et al. |
| 5,674,216 A | 10/1997 | Buell et al. |
| 5,702,551 A | 12/1997 | Huber et al. |
| 5,817,804 A | 10/1998 | Wolleb |
| 5,856,366 A | 1/1999 | Shiveley et al. |
| 5,897,545 A | 4/1999 | Kline et al. |
| 5,916,661 A | 6/1999 | Benson et al. |
| 5,957,908 A | 9/1999 | Kline et al. |
| 5,968,025 A | 10/1999 | Roe et al. |
| 6,107,537 A | 8/2000 | Elder et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,153,209 A | 11/2000 | Vega et al. |
| 6,160,028 A | 12/2000 | Dyer |
| 6,245,697 B1 * | 6/2001 | Conrad ............. C08F 220/18 428/304.4 |
| 6,410,129 B2 | 6/2002 | Zhang et al. |
| 6,426,444 B2 | 6/2002 | Roe et al. |
| 6,545,197 B1 | 4/2003 | Muller et al. |
| 6,586,652 B1 | 7/2003 | Roe et al. |
| 6,617,016 B2 | 9/2003 | Zhang et al. |
| 6,627,787 B1 | 9/2003 | Roe et al. |
| 6,825,393 B2 | 11/2004 | Roe et al. |
| 6,852,905 B2 | 2/2005 | Baker |
| 6,861,571 B1 | 3/2005 | Roe et al. |
| 7,432,413 B2 | 10/2008 | Roe et al. |
| 8,980,966 B2 | 3/2015 | Dörr et al. |
| 2003/0233082 A1 | 12/2003 | Kline et al. |
| 2004/0162536 A1 | 8/2004 | Becker et al. |
| 2004/0167486 A1 | 8/2004 | Busam et al. |
| 2005/0096614 A1 | 5/2005 | Perez et al. |
| 2005/0124954 A1 | 6/2005 | Adams et al. |
| 2007/0142798 A1 | 6/2007 | Goodlander et al. |
| 2007/0287983 A1 | 12/2007 | Lodge et al. |
| 2008/0132865 A1 | 6/2008 | Li et al. |
| 2008/0208154 A1 | 8/2008 | Oetjen et al. |
| 2008/0312617 A1 | 12/2008 | Hundorf et al. |
| 2010/0034995 A1 | 2/2010 | Tobita et al. |
| 2012/0222576 A1 | 9/2012 | McNeil et al. |
| 2012/0316526 A1 | 12/2012 | Rosati et al. |
| 2013/0072887 A1 | 3/2013 | LaVon et al. |
| 2013/0211356 A1 | 8/2013 | Nishikawa et al. |
| 2013/0306226 A1 | 11/2013 | Zink et al. |
| 2014/0295134 A1 | 10/2014 | Wood et al. |
| 2014/0295135 A1 | 10/2014 | Thompson, Jr. et al. |
| 2015/0080823 A1 | 3/2015 | Thompson et al. |
| 2015/0313770 A1 | 11/2015 | Hubbard, Jr. et al. |
| 2015/0335498 A1 | 11/2015 | Hubbard, Jr. et al. |
| 2015/0374561 A1 | 12/2015 | Hubbard, Jr. et al. |

* cited by examiner

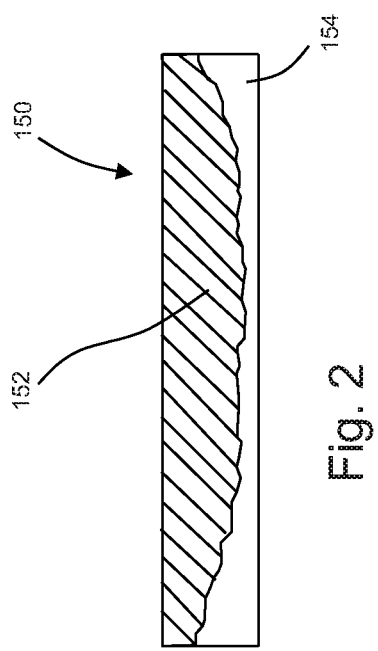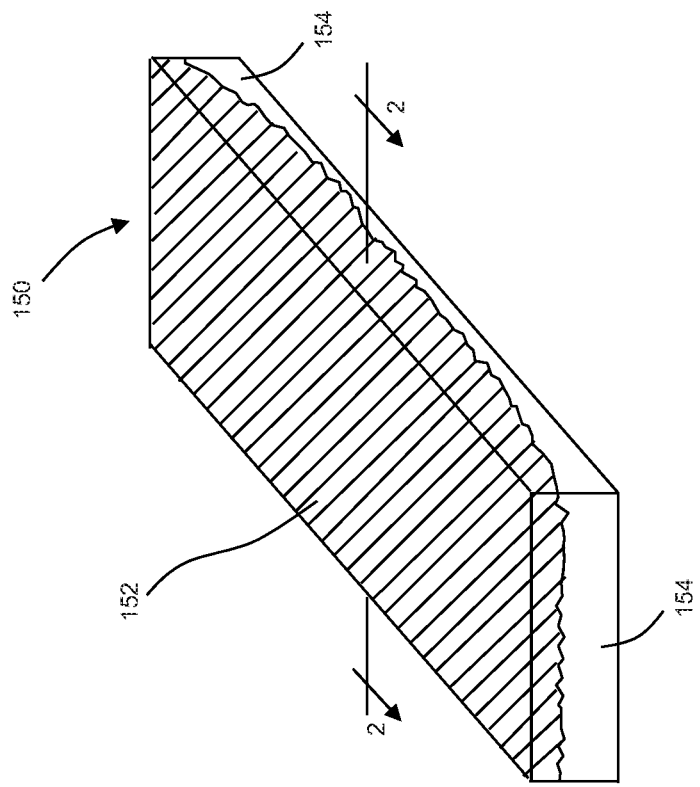

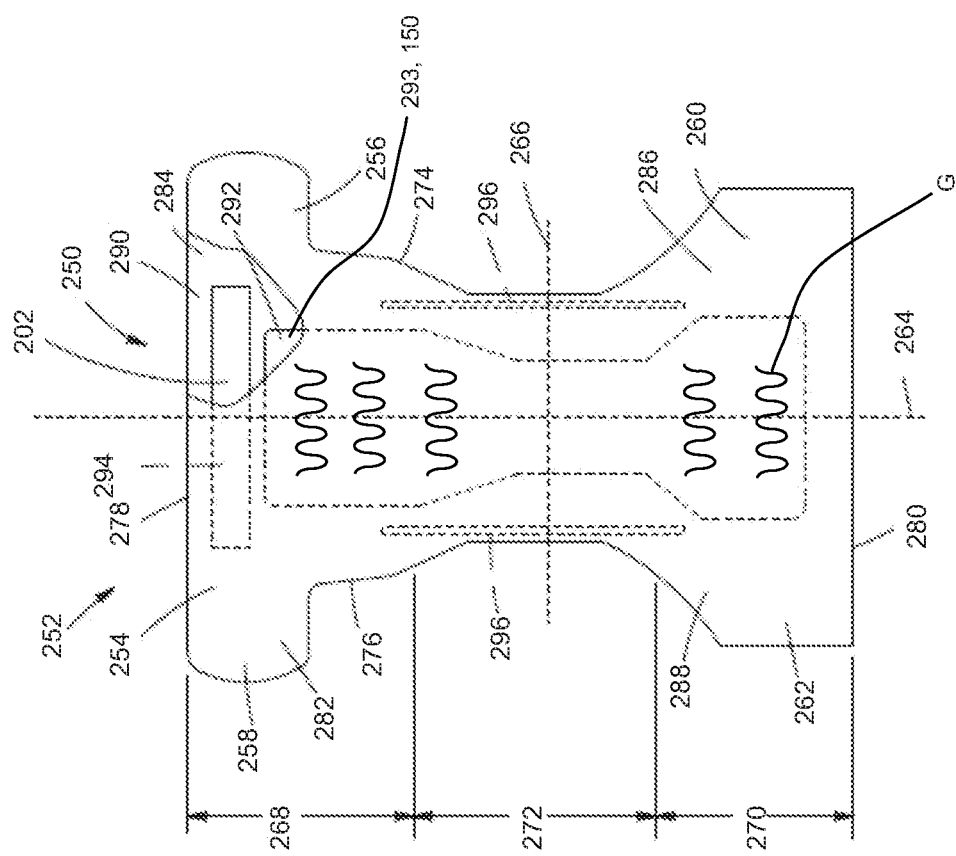

HETEROGENEOUS FOAM MATERIALS HAVING A GRAPHIC PRINTED THEREON

CROSS REFERENCE TO RELATED APPLICATIONS

This application claims the benefit of U.S. Provisional Application No. 62/153,535 filed on Apr. 28, 2015, which is incorporated herein by reference.

FIELD OF THE INVENTION

The present disclosure relates to absorbent foams comprising a hydrophilic, flexible, nonionic polymeric foam structure of interconnected open cells having a graphic printed thereon, and more particularly, to homogeneous or heterogeneous High Internal Phase Emulsion (HIPE) foams having a graphic printed thereon.

BACKGROUND OF THE INVENTION

An emulsion is a dispersion of one liquid in another liquid and generally is in the form of a water-in-oil mixture having an aqueous or water phase dispersed within a substantially immiscible continuous oil phase. Water-in-oil (or oil in water) emulsions having a high ratio of dispersed phase to continuous phase are known in the art as High Internal Phase Emulsions, also referred to as "HIPE" or HIPEs. At relatively high dispersed aqueous phase to continuous oil phase ratios the continuous oil phase becomes essentially a thin film separating and coating the droplet-like structures of the internal, dispersed aqueous phase. In certain HIPEs continuous oil phase comprises one or more polymerizable monomers. These monomers can be polymerized, forming a cellular structure, for example a foam, having a cell size distribution defined by the size distribution of the dispersed, aqueous phase droplets.

In some instances, HIPE foams may be configured such that upon contact with aqueous fluids, for example, bodily fluids such as urine and blood, can acquire, distribute, and store the aqueous fluids. As such, HIPE foams may be adapted for use in absorbent articles, such as feminine hygiene articles, diapers, pants, and adult incontinent products. In some instances, various HIPE foams are generally unaesthetically pleasing, lacking any graphic or visually pleasing appearance characteristic. Visual graphics are an important aspect of delivering against consumer needs by communicating a signal that a product will deliver against performance expectations as well as making the use of such products an enjoyable use experience. As such, HIPE foams with one or more graphics disposed thereon may be generally viewed as more appealing to consumers than those without graphics.

Printing graphics on HIPE foams presents various challenges. For example, because HIPEs may be configured to absorb aqueous fluids, inks solutions applied to such HIPE foams might be absorbed by the HIPE foams. Thus, the ink may penetrate into the interior of a HIPE foam, and as such, the resulting color intensity may be less than desired and may be less visible to a viewer. In addition, some inks may create problems, such as rub off issues, wherein ink from the HIPE foam rubs off and is deposited on the wearer's skin, panty surfaces, underwear surfaces, clothes, fabrics, or other materials.

The printing of inks on HIPE foams may also present other difficulties when considering the potential for a relatively high degree of dot gain on such materials (the spread of the ink from an initial/intended point of printing to surrounding areas). For example, a typical piece of paper that may be used for printing a book will have a dot gain of about 3% to about 4%, whereas a HIPE foam material may have potential for a much higher dot gain because of HIPE foam's ability to rapidly wick fluids. The higher dot gain would make it difficult to deliver against target color intensity levels and it would limit the color gamut available for consumer desired graphics; and make it difficult to deliver acceptable print quality, such as graphic or text clarity.

The printing of inks on HIPE foams may also have an impact on the absorbency properties of the material. For example, some inks may render the HIPE foam hydrophobic, thus degrading the ability to absorb body fluids when incorporated into an absorbent article. Thus, it may be desirable to reduce any detrimental impact by ink compositions on the absorbent capabilities of a printed HIPE foam.

Some absorbent article configurations include topsheet layers that overlay an absorbent core structure, wherein the topsheet layer is printed with graphics. In many such articles, the topsheet layer may be constructed from an apertured film material, a nonwoven, or combinations thereof. As such, printing on a topsheet layer on a converting line may result in blow through or bleed through of ink through the topsheet layer thereby resulting in ink contamination of parts on the converting line as well as unintended transfer of ink back onto products advancing through the converting line. In contrast, printing graphics on a HIPE foam used as an acquisition layer and/or an absorbent core layer that underlies a topsheet layer may help avoid the aforementioned negatives associated with printing inks on typical topsheet materials, especially when the printing operation is carried out on a disposable absorbent product converting line.

There is a need for a HIPE foam with graphics that overcomes the negatives described above. In addition, many consumers may prefer purchasing such HIPE foams and/or articles of manufacture having graphic designs printed thereon. Thus, there is an ongoing need for aesthetically appealing, HIPE foams where the color intensity and other performance properties of the web materials are not compromised as graphics or ink materials are added thereon.

SUMMARY OF THE INVENTION

The present disclosure relates to homogeneous or heterogeneous foams having a graphic printed thereon. As discussed herein, foam substrates, such as for example High Internal Phase Emulsion (HIPE) foam substrates may include a first surface and a second surface opposite the first surface, and one or more graphics may be printed directly on the first and/or second surfaces of the foam. The graphic may comprise ink positioned on the first and/or second surface, wherein the ink may penetrate into the foam below the surface on which the ink is applied. As such, the ink may reside on the foam and/or within the foam at various depths below the first and/or second surface.

In one form, a heterogeneous polymeric foam structure comprises: interconnected open-cells obtained from at least one water-in-oil emulsion; at least two distinct regions that differ by at least about 20% with regard to microcellular morphology; and a graphic printed on at least one of the two distinct regions.

In another form, a heterogeneous polymeric foam structure comprises: interconnected open-cells obtained from at least one water-in-oil emulsion; at least two distinct regions that differ by at least about 20% with regard to microcellular morphology; and a graphic printed on at least one of the two distinct regions, the graphic comprising L*a*b* color values, the graphic being defined by the CIELab coordinate values disposed inside the boundary described by the following system of equations:

$\{a^*=2.35 \text{ to } -20.19; b^*=79.81 \text{ to } 70.46\} \rightarrow b^*=0.415a^*+78.835$ $\{a^*=-20.19 \text{ to } -40.21; b^*=70.46 \text{ to } 53.48\} \rightarrow b^*=0.848a^*+87.584$ $\{a^*=-40.21 \text{ to } -51.26; b^*=53.48 \text{ to } 20.56\} \rightarrow b^*=2.979a^*+173.273$ $\{a^*=-51.26 \text{ to } -53.16; b^*=20.56 \text{ to } 2.64\} \rightarrow > b^*=9.432a^*+504.023$ $\{a^*=-53.16 \text{ to } -39.12; b^*=2.64 \text{ to } -30.65\} \rightarrow b^*=-2.371a^*-173.407$ $\{a^*=-39.12 \text{ to } -24.29; b^*=-30.65 \text{ to } -50.76\} \rightarrow b^*=-1.356a^*-83.698$ $\{a^*=-24.29 \text{ to } 5.66; b^*=-50.76 \text{ to } -44.78 \rightarrow b^*=0.200a^*-45.910$ $\{a^*=5.66 \text{ to } 46.22; b^*=-44.78 \text{ to } -21.00\} \rightarrow b^*=0.586a^*-48.098$ $\{a^*=46.22 \text{ to } 52.70; b^*=-21.00 \text{ to } -12.76\} \rightarrow b^*=1.272a^*-79.774$ $\{a^*=52.70 \text{ to } 55.98; b^*=-12.76 \text{ to } 9.83\} \rightarrow b^*=6.887a^*-375.715$ $\{a^*=55.98 \text{ to } 43.71; b^*=9.83 \text{ to } 47.92\} \rightarrow b^*=-3.104a^*+183.610$ $\{a^*=43.71 \text{ to } 2.35; b^*=47.92 \text{ to } 79.81\} \rightarrow b^*=-0.771a^*+81.622;$ and wherein L* is from 0 to 100.

In yet another form, a heterogeneous polymeric foam structure comprises: interconnected open-cells obtained from at least one water-in-oil emulsion; at least two distinct regions that differ by at least about 20% with regard to microcellular morphology; and a graphic printed on at least one of the two distinct regions, the graphic comprising L*a*b* color values, the graphic being defined by the CIELab coordinate values disposed inside the boundary described by the following system of equations:

$\{a^*=-5.66 \text{ to } -13.27; b^*=59.89 \text{ to } 57.29\} \rightarrow b^*=0.342a^*+61.824$ $\{a^*=-13.27 \text{ to } -25.02; b^*=57.29 \text{ to } 40.39\} \rightarrow b^*=1.438a^*+76.376$ $\{a^*=-25.02 \text{ to } -35.25; b^*=40.39 \text{ to } 14.23\} \rightarrow b^*=2.557a^*+104.371$ $\{a^*=-35.25 \text{ to } -35.55; b^*=14.23 \text{ to } -0.42\} \rightarrow > b^*=48.833a^*+1735.605$ $\{a^*=-35.55 \text{ to } -16.05; b^*=-0.42 \text{ to } -40.40\} \rightarrow b^*=-2.050a^*-73.307$ $\{a^*=-16.05 \text{ to } 5.30; b^*=-40.40 \text{ to } -32.69\} \rightarrow b^*=0.361a^*-34.604$ $\{a^*=5.30 \text{ to } 34.81; b^*=-32.69 \text{ to } -12.63\} \rightarrow b^*=0.680a^*-36.293$ $\{a^*=34.81 \text{ to } 39.33; b^*=-12.63 \text{ to } -5.99\} \rightarrow b^*=1.469a^*-63.767$ $\{a^*=39.33 \text{ to } 44.16; b^*=-5.99 \text{ to } 17.53\} \rightarrow b^*=4.870a^*-197.510$ $\{a^*=44.16 \text{ to } 42.52; b^*=17.53 \text{ to } 33.24\} \rightarrow b^*=-9.579a^*+440.550$ $\{a^*=42.52 \text{ to } 0.92; b^*=33.24 \text{ to } 58.23\} \rightarrow b^*=-0.601a^*+58.783$ $\{a^*=0.92 \text{ to } -5.66; b^*=58.23 \text{ to } 59.89\} \rightarrow b^*=-0.252a^*+58.462;$ and wherein L* is from 0 to 100.

In still another form, a heterogeneous polymeric foam structure comprises: interconnected open-cells obtained from at least one water-in-oil emulsion; at least two distinct regions that differ by at least about 20% with regard to microcellular morphology; a first surface; a second surface opposite the first surface; a graphic printed directly on the first surface, and wherein foam structure has a dry average ink adhesion rating of at least about 1.5 or greater.

In still another form, a heterogeneous polymeric foam structure comprises: interconnected open-cells obtained from at least one water-in-oil emulsion; at least two distinct regions that differ by at least about 20% with regard to microcellular morphology; a first surface; a second surface opposite the first surface; a graphic printed directly on the first surface, and wherein foam structure has a wet average ink adhesion rating of at least about 1.5 or greater.

In still another form, a polymeric foam structure comprises: interconnected open-cells obtained from at least one water-in-oil emulsion; a first surface; a second surface opposite the first surface; and a graphic printed on the first surface.

In still another form, a polymeric foam structure comprises: interconnected open-cells obtained from at least one water-in-oil emulsion; a first surface and a second surface opposite the first surface; and a graphic printed on the first surface, the graphic comprising L*a*b* color values, the graphic being defined by the CIELab coordinate values disposed inside the boundary described by the following system of equations:

$\{a^*=2.35 \text{ to } -20.19; b^*=79.81 \text{ to } 70.46\} \rightarrow b^*=0.415a^*+78.835$ $\{a^*=-20.19 \text{ to } -40.21; b^*=70.46 \text{ to } 53.48\} \rightarrow b^*=0.848a^*+87.584$ $\{a^*=-40.21 \text{ to } -51.26; b^*=53.48 \text{ to } 20.56\} \rightarrow b^*=2.979a^*+173.273$ $\{a^*=-51.26 \text{ to } -53.16; b^*=20.56 \text{ to } 2.64\} \rightarrow > b^*=9.432a^*+504.023$ $\{a^*=-53.16 \text{ to } -39.12; b^*=2.64 \text{ to } -30.65\} \rightarrow b^*=-2.371a^*-173.407$ $\{a^*=-39.12 \text{ to } -24.29; b^*=-30.65 \text{ to } -50.76\} \rightarrow b^*=-1.356a^*-83.698$ $\{a^*=-24.29 \text{ to } 5.66; b^*=-50.76 \text{ to } -44.78 \rightarrow b^*=0.200a^*-45.910$ $\{a^*=5.66 \text{ to } 46.22; b^*=-44.78 \text{ to } -21.00\} \rightarrow b^*=0.586a^*-48.098$ $\{a^*=46.22 \text{ to } 52.70; b^*=-21.00 \text{ to } -12.76\} \rightarrow b^*=1.272a^*-79.774$ $\{a^*=52.70 \text{ to } 55.98; b^*=-12.76 \text{ to } 9.83\} \rightarrow b^*=6.887a^*-375.715$ $\{a^*=55.98 \text{ to } 43.71; b^*=9.83 \text{ to } 47.92\} \rightarrow b^*=-3.104a^*+183.610$ $\{a^*=43.71 \text{ to } 2.35; b^*=47.92 \text{ to } 79.81\} \rightarrow b^*=-0.771a^*+81.622;$ and wherein L* is from 0 to 100.

In still another form, a polymeric foam structure comprises: interconnected open-cells obtained from at least one water-in-oil emulsion; a first surface and a second surface opposite the first surface; and a graphic printed on the first surface, the graphic comprising L*a*b* color values, the graphic being defined by the CIELab coordinate values disposed inside the boundary described by the following system of equations:

$\{a^*=-5.66 \text{ to } -13.27; b^*=59.89 \text{ to } 57.29\} \rightarrow b^*=0.342a^*+61.824$ $\{a^*=-13.27 \text{ to } -25.02; b^*=57.29 \text{ to } 40.39\} \rightarrow b^*=1.438a^*+76.376$ $\{a^*=-25.02 \text{ to } -35.25; b^*=40.39 \text{ to } 14.23\} \rightarrow b^*=2.557a^*+104.371$ $\{a^*=-35.25 \text{ to } -35.55; b^*=14.23 \text{ to } -0.42\} \rightarrow b^*=48.833a^*+1735.605$ $\{a^*=-35.55 \text{ to } -16.05; b^*=-0.42 \text{ to } -40.40\} \rightarrow b^*=-2.050a^*-73.307$ $\{a^*=-16.05 \text{ to } 5.30; b^*=-40.40 \text{ to } -32.69\} \rightarrow b^*=0.361a^*-34.604$ $\{a^*=5.30 \text{ to } 34.81; b^*=-32.69 \text{ to } -12.63 \rightarrow b^*=0.680a^*-36.293$ $\{a^*=34.81 \text{ to } 39.33; b^*=-12.63 \text{ to } -5.99\} \rightarrow b^*=1.469a^*-63.767$ $\{a^*=39.33 \text{ to } 44.16; b^*=-5.99 \text{ to } 17.53\} \rightarrow b^*=4.870a^*-197.510$ $\{a^*=44.16 \text{ to } 42.52; b^*=17.53 \text{ to } 33.24\} \rightarrow b^*=-9.579a^*+440.550$ $\{a^*=42.52 \text{ to } 0.92; b^*=33.24 \text{ to } 58.23\} \rightarrow b^*=-0.601a^*+58.783$ $\{a^*=0.92 \text{ to } -5.66; b^*=58.23 \text{ to } 59.89\} \rightarrow b^*=-0.252a^*+58.462;$ and wherein L* is from 0 to 100.

In still another form, a polymeric foam structure comprises: interconnected open-cells obtained from at least one water-in-oil emulsion; a first surface; a second surface opposite the first surface; a graphic printed directly on the first surface, and wherein foam structure has a dry average ink adhesion rating of at least about 1.5 or greater.

In still another form, a polymeric foam structure comprises: interconnected open-cells obtained from at least one water-in-oil emulsion; a first surface; a second surface opposite the first surface; a graphic printed directly on the first surface, and wherein foam structure has a wet average ink adhesion rating of at least about 1.5 or greater.

In still another form, a polyurethane foam structure comprises: interconnected open-cells obtained from a reaction product of at least one polyol component and a diisocyanate component; a first surface; a second surface opposite the first surface; and a graphic printed on the first surface.

In still another form, a hydrophilic, flexible, nonionic polymeric foam structure comprises: interconnected open-cells; a first surface; a second surface opposite the first surface; and a graphic printed on the first surface.

BRIEF DESCRIPTION OF THE DRAWINGS

FIG. 1 is a perspective view of a sheet of HIPE foam showing discrete regions layered in a z-direction (thickness) of the foam.

FIG. 2 is a cross sectional view of the HIPE foam shown in FIG. 1 taken along the sectional line 2-2.

FIG. 9 is a top plan view of a disposable absorbent article in the form of a diaper including an absorbent assembly having a component with graphics printed thereon.

DETAILED DESCRIPTION OF THE INVENTION

Figure 3:
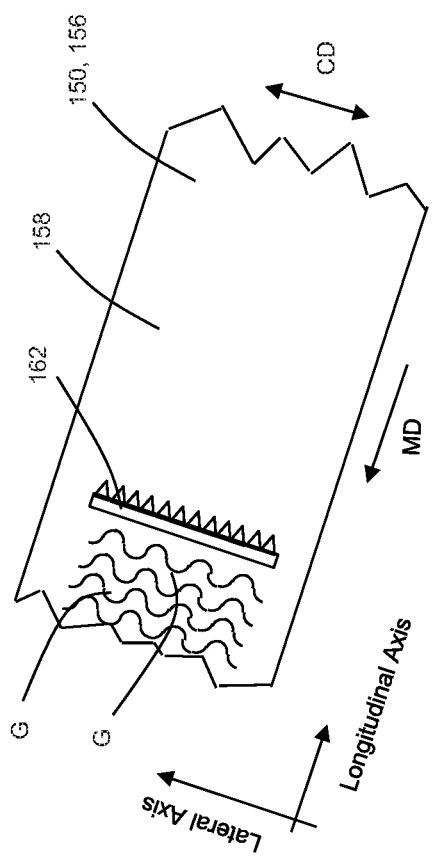
FIG. 3 shows one example of how graphics may be printed on a HIPE foam substrate.

The following term explanations may be useful in understanding the present disclosure:

"Absorbent article" is used herein to refer to consumer products whose primary function is to absorb and retain soils and wastes. An absorbent article can comprise a disposable diaper, disposable pant, an insert for diaper with a reusable outer cover, a sanitary napkin, a tampon, an adult incontinent diaper, an adult incontinent pad, or an adult incontinent pant. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Base Color," as used herein, refers to a color that is used in the halftoning printing process as the foundation for creating additional colors. In some non-limiting embodiments, a base color is provided by a colored ink. Non-limiting examples of base colors may selected from the group consisting of: cyan, magenta, yellow, black, red, green, and blue-violet.

"Black", as used herein, refers to a color and/or base color which absorbs wavelengths in the entire spectral region of from about 380 nm to about 740 nm.

"Blue" or "Blue-violet", as used herein, refers to a color and/or base color which have a local maximum reflectance in the spectral region of from about 390 nm to about 490 nm.

"Cyan", as used herein, refers to a color and/or base color which have a local maximum reflectance in the spectral region of from about 390 nm to about 570 nm. In some embodiments, the local maximum reflectance is between the local maximum reflectance of the blue or blue-violet and green local maxima.

"Dot gain" is a phenomenon in printing which causes printed material to look darker, less sharp, and/or fuzzier than intended. It is caused by halftone dots growing in area between the original image ("input halftone") and the image finally printed upon the web material ("output halftone").

An "ink" is a liquid containing coloring matter, for imparting a particular hue to web materials. An ink may include dyes, pigments, organic pigments, inorganic pigments, and/or combinations thereof. A non-limiting example of an ink would encompass spot colors.

Additional non-limiting examples of inks include inks having white color. Additional non-limiting examples of inks include hot melt inks.

"Green", as used herein, refers to a color and/or base color which have a local maximum reflectance in the spectral region of from about 491 nm to about 570 nm.

"Halftone" or "halftoning" as used herein, sometimes referred to as "screening," is a printing technique that allows for less-than-full saturation of the primary colors. In halftoning, relatively small dots of each primary color are printed in a pattern small enough such that the average human observer perceives a single color. For example, magenta printed with a 20% halftone will appear to the average observer as the color pink. The reason for this is because, without wishing to be limited by theory, the average observer may perceive the tiny magenta dots and white paper between the dots as lighter, and less saturated, than the color of pure magenta ink.

"Hue" is the relative red, yellow, green, and blue-violet in a particular color. A ray can be created from the origin to any color within the two-dimensional a*b* space. Hue is the angle measured from 0° (the positive a* axis) to the created ray. Hue can be any value of between 0° to 360°. Lightness is determined from the L* value with higher values being more white and lower values being more black.

"Lab Color" or "L*a*b* Color Space," as used herein, refers to a color model that is used by those of skill in the art to characterize and quantitatively describe perceived colors with a relatively high level of precision. More specifically, CIELab may be used to illustrate a gamut of color because L*a*b* color space has a relatively high degree of perceptual uniformity between colors. As a result, L*a*b* color space may be used to describe the gamut of colors that an ordinary observer may actually perceive visually.

"Magenta", as used herein, refers to a color and/or base color which have a local maximum reflectance in the spectral region of from about 390 nm to about 490 nm and 621 nm to about 740 nm.

"Process Printing," as used herein, refers to the method of providing color prints using at least three of the primary of colors cyan, magenta, yellow and black. Each layer of color is added over a base substrate. In some embodiments, the base substrate is white or off-white in color. With the addition of each layer of color, certain amounts of light are absorbed (those of skill in the printing arts will understand that the inks actually "subtract" from the brightness of the white background), resulting in various colors. CMY (cyan, magenta, yellow) are used in combination to provide additional colors. Non-limiting examples of such colors are red, green, and blue. K (black) is used to provide alternate shades and pigments. One of skill in the art will appreciate that CMY may alternatively be used in combination to provide a black-type color.

"Red", as used herein, refers to a color and/or base color which has a local maximum reflectance in the spectral region of from about 621 nm to about 740 nm.

"Resultant Color," as used herein, refers to the color that an ordinary observer perceives on the finished product of a halftone printing process. As exemplified herein, the resultant color of magenta printed at a 20% halftone is pink.

"Yellow", as used herein, refers to a color and/or base color which have a local maximum reflectance in the spectral region of from about 571 nm to about 620 nm.

The term "graphic" refers to images or designs that are constituted by a figure (e.g., a line(s)), a symbol or character, a color difference or transition of at least two colors, or the like. A graphic may include an aesthetic image or design that can provide certain benefit(s) when viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink or spot colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

"Different in terms of graphic design" means that graphics are intended to be different when viewed by users or consumers with normal attentions. Thus, two graphics having a graphic difference(s) which are unintentionally caused due to a problem(s) or an error(s) in a manufacture process, for example, are not different from each other in terms of graphic design.

"Standard" or "standardized" refers to graphics, products, and/or articles that have the same aesthetic appearance without intending to be different from each other.

The term "custom" or "customized" refers to graphics, products, and/or articles that are changed to suit a small demographic, region, purchaser, customer, or the like. Custom graphics may be selected from a set of graphics. For example, custom graphics may include animal depictions selected from groups of animals, such as farm animals, sea creatures, birds, and the like. In other examples, custom graphics may include nursery rhymes and the like. In one scenario, custom products or articles may be created by a purchaser of such products or articles wherein the purchaser selects graphics for the articles or products from a set of graphics offered by a manufacturer of such articles or products. Custom graphics may also include "personalized" graphics, which may be graphics created for a particular purchaser. For example, personalized graphics may include a person's name alone or in combination with a design.

The present disclosure relates to homogeneous or heterogeneous foams, and more particularly, to High Internal Phase Emulsion (HIPE) foams having a graphic printed thereon. As discussed below, a HIPE foam substrate may include a first surface and a second surface opposite the first surface, and one or more graphics may be printed directly on the first and/or second surfaces of the HIPE foam. In some embodiments, the graphic comprises ink positioned on the first and/or second surface. It is also to be appreciated that the ink may penetrate into the HIPE foam below the surface on which the ink is applied. As such, the ink may reside on the HIPE foam and/or within the HIPE foam at various depths below the first and/or second surface. In some embodiments, the graphics may be applied such that the HIPE foams have various wet and/or dry ink adhesion ratings. In addition, a graphic may be printed directly on the HIPE foam such that the graphic can be defined by the CIELab coordinate values disposed inside the boundary described by systems of equations.

It is to be appreciated that the HIPE foams disclosed herein including graphics printed thereon may be used as absorbent core materials in absorbent articles, such as feminine hygiene articles, for example pads, pantiliners, and tampons; disposable diapers; incontinence articles, for example pads, adult diapers, adult pants, homecare articles, for example wipes, pads, towels; and beauty care articles, for example pads, wipes, and skin care articles, such as used for pore cleaning. To help provide additional context to the subsequent discussion of printing graphics on HIPE foams, the following provides a description of HIPE foams that may be printed in accordance with the methods disclosed herein.

A High Internal Phase Emulsion (HIPE) comprises two phases. One phase is a continuous oil phase comprising monomers that are polymerized to form a HIPE foam and an emulsifier to help stabilize the HIPE. The oil phase may also include one or more photoinitiators. The monomer component may be present in an amount of from about 80% to about 99%, and in certain embodiments from about 85% to about 95% by weight of the oil phase. The emulsifier component, which is soluble in the oil phase and suitable for forming a stable water-in-oil emulsion may be present in the oil phase in an amount of from about 1% to about 20% by weight of the oil phase. The emulsion may be formed at an emulsification temperature of from about 20° C. to about 130° C. and in certain embodiments from about 50° C. to about 100° C.

In general, the monomers will include from about 20% to about 97% by weight of the oil phase at least one substantially water-insoluble monofunctional alkyl acrylate or alkyl methacrylate. For example, monomers of this type may include $C_4$-$C_{18}$ alkyl acrylates and $C_2$-$C_{18}$ methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also comprise from about 2% to about 40%, and in certain embodiments from about 10% to about 30%, by weight of the oil phase, a substantially water-insoluble, polyfunctional crosslinking alkyl acrylate or methacrylate. This crosslinking comonomer, or crosslinker, is added to confer strength and resilience to the resulting HIPE foam. Examples of crosslinking monomers of this type comprise monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,1 2-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate: acrylate group in the mixed crosslinker may be varied from 50:50 to any other ratio as needed.

Any third substantially water-insoluble comonomer may be added to the oil phase in weight percentages of from about 0% to about 15% by weight of the oil phase, in certain embodiments from about 2% to about 8%, to modify properties of the HIPE foams. In certain embodiments, "toughening" monomers may be desired which impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers can be used to slow down the polymerization rate of a HIPE. Examples of monomers of this type comprise styrene and vinyl chloride.

The oil phase may further contain an emulsifier used for stabilizing the HIPE. Emulsifiers used in a HIPE can include: (a) sorbitan monoesters of branched $C_{16}$-$C_{24}$ fatty acids; linear unsaturated $C_{16}$-$C_{22}$ fatty acids; and linear saturated $C_{12}$-$C_{14}$ fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of -branched $C_{16}$-$C_{24}$ fatty acids, linear unsaturated $C_{16}$-$C_{22}$ fatty acids, or linear saturated $C_{12}$-$C_{14}$ fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched $C_{16}$-$C_{24}$ alcohols, linear unsaturated $C_{16}$-$C_{22}$ alcohols, and linear saturated $C_{12}$-$C_{14}$ alcohols, and mixtures of these emulsifiers. See U.S. Pat. Nos. 5,387,207 and 5,500,451. Another emulsifier that may be used is polyglycerol succinate (PGS), which is formed from an alkyl succinate, glycerol, and triglycerol.

Such emulsifiers, and combinations thereof, may be added to the oil phase so that they comprise between about 1% and about 20%, in certain embodiments from about 2% to about 15%, and in certain other embodiments from about 3% to about 12% by weight of the oil phase. In certain embodiments, coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain $C_{12}$-$C_{22}$ dialiphatic quaternary ammonium salts, short chain $C_1$-$C_4$ dialiphatic quaternary ammonium salts, long chain $C_{12}$-$C_{22}$ dialkoyl(alkenoyl)-2-hydroxyethyl, short chain $C_1$-$C_4$ dialiphatic quaternary ammonium salts, long chain $C_{12}$-$C_{22}$ dialiphatic imidazolinium quaternary ammonium salts, short chain $C_1$-$C_4$ dialiphatic imidazolinium quaternary ammonium salts, long chain $C_{12}$-$C_{22}$ monoaliphatic benzyl quaternary ammonium salts, long chain $C_{12}$-$C_{22}$ dialkoyl(alkenoyl)-2-aminoethyl, short chain $C_1$-$C_4$ monoaliphatic benzyl quaternary ammonium salts, short chain $C_1$-$C_4$ monohydroxyaliphatic quaternary ammonium salts. In certain embodiments, ditallow dimethyl ammonium methyl sulfate (DTDMAMS) may be used as a coemulsifier.

Photoinitiators may comprise between about 0.05% and about 10%, and in certain embodiments between about 0.2% and about 10% by weight of the oil phase. Lower amounts of photoinitiator allow light to better penetrate the HIPE foam, which can provide for polymerization deeper into the HIPE foam. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. The photoinitiators may absorb UV light at wavelengths of about 200 nanometers (nm) to about 800 nm, in certain embodiments about 200 nm to about 350 nm. If the photoinitiator is in the oil phase, suitable types of oil-soluble photoinitiators include benzyl ketals, α-hydroxyalkyl phenones, α-amino alkyl phenones, and acylphospine oxides. Examples of photoinitiators include 2,4,6-[trimethylbenzoyldiphosphine] oxide in combination with 2-hydroxy-2-methyl-1-phenylpropan-1-one (50:50 blend of the two is sold by Ciba Speciality Chemicals, Ludwigshafen, Germany as DAROCUR® 4265); benzyl dimethyl ketal (sold by Ciba Geigy as IRGACURE 651); α-,α-dimethoxy-α-hydroxy acetophenone (sold by Ciba Speciality Chemicals as DAROCUR® 1173); 2-methyl-1-[4-(methyl thio) phenyl]-2-morpholino-propan-1-one (sold by Ciba Speciality Chemicals as IRGACURE® 907); 1-hydroxycyclohexyl-phenyl ketone (sold by Ciba Speciality Chemicals as IRGACURE® 184); bis(2,4,6-trimethylbenzoyl)-phenylphosphineoxide (sold by Ciba Speciality Chemicals as IRGACURE 819); diethoxyacetophenone, and 4-(2-hydroxyethoxy)phenyl-(2-hydroxy-2-methylpropyl) ketone (sold by Ciba Speciality Chemicals as IRGACURE® 2959); and Oligo [2-hydroxy-2-methyl-1-[4-(1-methylvinyl) phenyl]propanone] (sold by Lamberti spa, Gallarate, Italy as ESACURE® KIP EM.

The dispersed aqueous phase of a HIPE comprises water, and may also comprise one or more components, such as initiator, photoinitiator, or electrolyte, wherein in certain embodiments, the one or more components are at least partially water soluble.

One component of the aqueous phase may be a water-soluble electrolyte. The water phase may contain from about 0.2% to about 40%, in certain embodiments from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte can include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Another component that may be present in the aqueous phase is a water-soluble free-radical initiator. The initiator can be present at up to about 20 mole percent based on the total moles of polymerizable monomers present in the oil phase. In certain embodiments, the initiator is present in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine)dihydrochloride, and other suitable azo initiators. In certain embodiments, to reduce the potential for premature polymerization which may clog the emulsification system, addition of the initiator to the monomer phase may be just after or near the end of emulsification.

Photoinitiators present in the aqueous phase may be at least partially water soluble and may comprise between about 0.05% and about 10%, and in certain embodiments between about 0.2% and about 10% by weight of the oil phase. Lower amounts of photoinitiator allow light to better penetrate the HIPE foam, which can provide for polymerization deeper into the HIPE foam. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. The photoinitiators may absorb UV light at wavelengths of from about 200 nanometers (nm) to about 800 nm, in certain embodiments from about 200 nm to about 350 nm, and in certain embodiments from about 350 nm to about 450 nm. If the photoinitiator is in the aqueous phase, suitable types of water-soluble photoinitiators include benzophenones, benzils, and thioxanthones. Examples of photoinitiators include 2,2'-Azobis [2-(2-imidazolin-2-yl)propane]dihydrochloride; 2,2'-Azobis [2-(2-imidazolin-2-yl)propane]disulfate dehydrate; 2,2'-Azobis (1-imino-1-pyrrolidino-2-ethylpropane)dihydrochloride; 2,2'-Azobis [2-methyl-N-(2-hydroxyethyl)propionamide]; 2,2'-Azobis(2-methylpropionamidine)dihydrochloride; 2,2'-dicarboxymethoxydibenzalacetone, 4,4'-dicarboxymethoxydibenzalacetone, 4,4'-dicarboxymethoxydibenzalcyclohexanone, 4-dimethylamino-4'-carboxymethoxydibenzalacetone; and 4,4'-disulphoxymethoxydibenzalacetone. Other suitable photoinitiators that can be used are listed in U.S. Pat. No. 4,824,765.

In addition to the previously described components, other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler particles, for example starch, titanium dioxide, carbon black, or calcium carbonate; fibers; chain transfer agents; odor absorbers, for example activated carbon particulates; dissolved polymers; dissolved oligomers; and the like.

Regardless of whether a heterogeneous foam is relatively hydrophobic, or is a hydrophilic foam suitable for aqueous fluid absorption, the foam may have one or more distinct regions. Such distinct regions may differ with regard to one or more of foam density, polymer composition, specific surface area, or microcellular morphology (e.g., cell size, shape, or distribution, or hole size). And regardless of whether a homogeneous foam is relatively hydrophobic, or is a hydrophilic foam suitable for aqueous fluid absorption, the foam will have a distinct region, characterized by a foam density, polymer composition, specific surface area, or microcellular morphology (e.g., cell size, shape, or distribution, or hole size).

Foam cells, and especially cells that are formed by polymerizing a monomer-containing oil phase that surrounds relatively monomer-free water-phase droplets, may be substantially spherical in shape. The size or "diameter" of such spherical cells is a parameter that may be used to characterize such foams. Similarly, the diameter of holes connecting the cells may be used to characterize such foams. Since cells and holes between cells in a given sample of polymeric foam will not necessarily be the same size, a mean cell size and/or a mean hole size may be specified. For foams described herein, each region may possess a different mean cell size and/or a different hole size. A number of techniques may be used to determine the mean cell size and mean hole size of foams. For example, some techniques for determining cell size and hole size in foams involve a simple measurement based on the scanning electron photomicrograph of a foam sample, for example, such as the Method for Measuring Mean Cell Size provided below.

Some foam embodiments herein may have one or more regions suitable for acquisition of fluid and may have a mean cell size of from about 20 to about 200 µm; from about 50 to about 190 µm; or from about 80 to about 180 µm; and may have a mean hole size of from about 5 to about 45 µm; from about 8 to about 40 µm; or from about 20 to about 35 µm. These foams may also have one or more fluid storage regions that may have a mean cell size of not more than about 50 µm; from about 5 to about 35 µm; and may have a mean hole size not more than about 10 µm; or from about 1 to about 7 µm.

"Foam density," which is characterized in grams of foam per cubic centimeter of foam volume in air, is specified herein on a dry basis. Foam density may be measured on the entire foam even when distinct regions may have distinct values which may be measured separately. The aggregate density of a foam having two or more distinct regions of polymer with different densities would be the volume averaged densities from each area. In some embodiments, the aggregate density may range between about 0.04 g/cc and 0.01 g/cc, while the densities of the distinct regions may vary. For example, regions of relatively low density may be between about 0.02 and 0.005 g/cc. And regions of relatively high density may be between about 0.05 and 0.02 g/cc. The procedure for measuring aggregate foam density is described in U.S. Pat. No. 5,387,207. The amount of absorbed water-soluble residual materials, such as for example, residual salts and liquid left in the foam, after HIPE polymerization, washing and/or hydrophilization, is disregarded in calculating and expressing foam density. Foam density does include, however, other water-insoluble residual materials such as emulsifiers present in the polymerized foam. Such residual materials can contribute significant mass to the foam material.

As previously mentioned, HIPE foam is produced from the polymerization of the monomers comprising the continuous oil phase of a HIPE. In some embodiments, HIPE foams may have one or more layers, and may be either homogeneous or heterogeneous polymeric open-celled foams. Homogeneity and heterogeneity relate to distinct layers within the same HIPE foam, which are similar in the case of homogeneous HIPE foams or which differ in the case of heterogeneous HIPE foams. A heterogeneous HIPE foam may contain at least two distinct layers that differ with regard to their chemical composition, physical properties, or both; for example layers may differ with regard to one or more of foam density, polymer composition, specific surface area, or cell size (also referred to as pore size). For example, for a HIPE foam if the difference relates to cell size, the average cell size in each layer may differ by at least about 20%, in certain embodiments by at least about 35%, and in still other embodiments by at least about 50%. In another example, if the differences in the layers of a HIPE foam relate to density, the densities of the layers may differ by at least about 20%, in certain embodiments by at least about 35%, and in still other embodiments by at least about 50%. For instance, if one layer of a HIPE foam has a density of 0.020 g/cc, another layer may have a density of at least about 0.024 g/cc or less than about 0.016 g/cc, in certain embodiments at least about 0.027 g/cc or less than about 0.013 g/cc, and in still other embodiments at least about 0.030 g/cc or less than about 0.010 g/cc. If the differences between the layers are related to the chemical composition of the HIPE or HIPE foam, the differences may reflect a relative amount difference in at least one monomer component, for example by at least about 20%, in certain embodiments by at least about 35%, and in still further embodiments by at least about 50%. For instance, if one layer of a HIPE or HIPE foam is composed of about 10% styrene in its formulation, another layer of the HIPE or HIPE foam should be composed of at least about 12%, and in certain embodiments of at least about 15%.

A HIPE foam having separate layers formed from differing HIPEs, as explained in more detail below, provides a HIPE foam with a range of desired performance characteristics. For example, a HIPE foam comprising a first and second foam layer, wherein the first foam layer has a relatively larger cell size, than the second layer, when used in an absorbent article may more quickly absorb incoming fluids than the second layer. By way of example when used in an absorbent article, the first foam layer may be layered over the second foam layer having relatively smaller cell sizes, as compared to the first foam layer, which exert more capillary pressure and drain the acquired fluid from the first foam layer, restoring the first foam layer's ability to acquire more fluid. HIPE foam cell sizes may range in mean cell diameter of from 1 to 200 µm and in certain embodiments may be less than 100 µm. HIPE foams having two major parallel surfaces may be from 0.05 to 10 mm thick, and in certain embodiments 8 mm or less. The desired thickness of a HIPE will depend on the materials used to form the HIPE, the speed at which a HIPE is extruded on a belt, and the intended use of the resulting HIPE foam.

The HIPE foams may be relatively open-celled, which refers to the individual cells or pores of the HIPE foam being in substantially unobstructed communication with adjoining cells. The cells in such substantially open-celled HIPE foam structures have intercellular openings or windows that are large enough to permit ready fluid transfer from one cell to another within the HIPE foam structure. For purpose of the present disclosure, a HIPE foam is considered "open-celled"

if at least about 80% of the cells in the HIPE foam that are at least 1 µm in mean cell size are in fluid communication with at least one adjoining cell.

In addition to being open-celled, in certain embodiments HIPE foams are sufficiently hydrophilic to permit the HIPE foam to absorb aqueous fluids, for example the internal surfaces of a HIPE foam may be rendered hydrophilic by residual hydrophilizing surfactants or salts left in the HIPE foam following polymerization, by selected post-polymerization HIPE foam treatment procedures (as described hereafter), or combinations of both.

In certain embodiments, for example when used in certain absorbent articles, a HIPE foam may be flexible and exhibit an appropriate glass transition temperature (Tg). The Tg represents the midpoint of the transition between the glassy and rubbery states of the polymer. In general, HIPE foams that have a higher Tg than the temperature of use can be very strong but will also be rigid and potentially prone to fracture. In certain embodiments, regions of the HIPE foams which exhibit either a relatively high Tg or excessive brittleness will be discontinuous. Since these discontinuous regions will also generally exhibit high strength, they can be prepared at lower densities without compromising the overall strength of the HIPE foam.

HIPE foams intended for applications requiring flexibility may contain at least one continuous region having a Tg as low as possible, so long as the overall HIPE foam has acceptable strength at in-use temperatures. In certain embodiments, the Tg of this region will be less than about 30° C. for foams used at about ambient temperature conditions, in certain other embodiments less than about 20° C. For HIPE foams used in applications wherein the use temperature is higher or lower than ambient, the Tg of the continuous region may be no more than 10° C. greater than the use temperature, and in certain embodiments the same as use temperature, and in further embodiments about 10° C. less than use temperature wherein flexibility is desired. Accordingly, monomers may be selected as much as possible that provide corresponding polymers having lower Tg's.

In some embodiments, a heterogeneous foam may comprise a heterogeneous mass layer, such as described for example in U.S. Patent Application No. 61/988,565, filed May 5, 2014; U.S. Patent Application No. 62/115,921, filed Feb. 13, 2015; and U.S. Patent Application No. 62/018,212, filed on Jun. 27, 2014, which are all incorporated herein by reference. In some embodiments, the heterogeneous foam may comprise a heterogeneous mass comprising fibers and one or more discrete portions of HIPE foam that are immobilized in the heterogeneous mass. The open cell foam pieces are considered discrete in that the open cell foam pieces are not continuous throughout the entire heterogeneous mass. In some embodiments, the fibers may be part of a web such as, for example, nonwoven, a fibrous structure, an airlaid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are layered combinations thereof.

It is to be appreciated that the HIPE foams herein may include discrete regions with printed graphics. In some embodiments, a heterogeneous foam may include at least two distinct regions wherein a first region comprises a mean cell size of not more than about 50 µm; and a second region comprises a mean cell size from about 20 µm to about 200 µm. It is also to be appreciated that the discrete regions may be arranged in various ways within a HIPE foam, such as disclosed in U.S. Pat. No. 5,817,804. FIGS. 1 and 2 show an example of a HIPE foam 150 where the distinct regions are layered in the z-direction. More particularly, FIG. 1 is a perspective view of a foam 150 including a first region 152 and a second region 154, and FIG. 2 is a side view of the foam 150 including the first region 152 and the second region 154. As discussed below, the illustrated foam 150 may be configured as an absorbent material for use in an absorbent article, such as a diaper. Exemplary descriptions of various diaper components are provided below with reference to FIGS. 9-11. In some absorbent article configurations, the first region 152 may be utilized as an acquisition material, and the second region 154 may be utilized as a storage material. In such a configuration, the first region 152 may have a relatively lower specific surface area per volume than the second region 154, which will allow the second region 154 to drain fluid from first region 152. It is to be appreciated that a foam 150 having layered regions, such as being layered in the z-direction, may be formed in various ways. For example, such layered foams may be formed by pouring an emulsion to form region 154 in a mold, and simultaneously or sequentially adding a second emulsion to form region 152.

Figure 5:
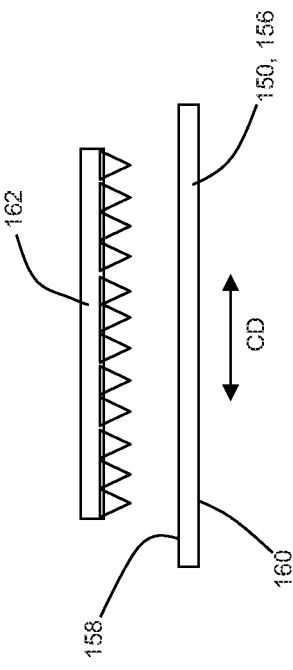
FIG. 5 is a plan view of the foam of FIG. 3 looking in the machine direction MD.
Figure 4:
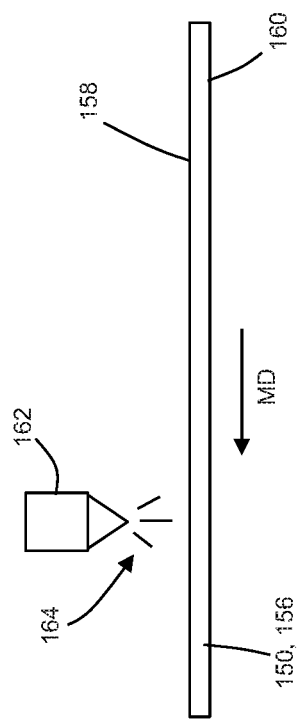
FIG. 4 is a plan view of the foam of FIG. 3 looking in the cross direction CD.

As previously mentioned, graphics may be printed on substrates or sheets of HIPE foam structures according the present disclosure. Printing may be characterized as an industrial process in which a graphic is reproduced on a sheet. FIGS. 3-5 show one example of how graphics G may be printed on a HIPE foam 150 described above in the form of a sheet 156 including a first surface 158 and a second surface 160 opposite the first surface 158. A plurality of graphics G in FIG. 3 is schematically represented by a series of curved or wavy line shapes. To provide a frame of reference for the present discussion, the sheet 156 is shown in FIG. 3 with a longitudinal axis and a lateral axis. The longitudinal axis also corresponds with what may be referred to as the machine direction MD of the sheet 156, and the lateral axis corresponds with what may be referred to as the cross direction CD of the sheet 156. As shown in FIGS. 3-5, graphics G may be printed on a first surface 158 of the sheet 156 by advancing the sheet in the longitudinal direction relative to a printing station 162 while the printing station 162 prints ink 164 onto the first surface 158 to form the graphics G. It is to be appreciated that the printing station may also be configured to move relative to the substrate while printing. For example, the printing station may move back and forth in lateral directions relative to the substrate while printing the graphics.

It is to be appreciated that the printing station 162 may be configured in various ways and may include various types of printing accessories. For example, in some embodiments, the printing station may include a printer in the form of an ink-jet printer. Ink-jet printing is a non-impact dot-matrix printing technology in which droplets of ink are jetted from a small aperture directly to a specified position on a media to create a graphic. Three examples of inkjet technologies include thermal bubble or bubble jet, continuous inkjet, and piezoelectric. Thermal bubble uses heat and jet the ink, while piezoelectric uses a crystal and an electric charge to apply the ink. In some configurations, the printing station may include a corona treater, which may be positioned upstream of the printer. The corona treater may be utilized to increase the surface energy of the surface of substrates or sheets of HIPE foam structures to be printed. In some configurations, the printing station may also include an ink curing apparatus. In some configurations, the ink curing apparatus may be in the form of an ultraviolet (UV) light source that may include one or more ultraviolet (UV) lamps, which may be positioned downstream of the printer to help cure inks deposited onto the substrates or sheets of HIPE foam structures from the printer to form the graphics. In some configurations, the ink curing apparatus may also include an infrared (IR) dryer light source that may include one or more infrared (IR) lamps, which may be positioned downstream of the printer to help dry water-based or solvent-based inks deposited onto the substrates or sheets of HIPE foam structures from the printer to form the graphics. In some configurations, the ink curing apparatus may include an electron beam (EB or e-beam) generator that may include one or more e-beam electrodes, which may be positioned downstream of the printer to help cure inks deposited onto the substrates or sheets of HIPE foam structures from the printer to form the graphics.

It is it to be appreciated that various types of printing processes may be used to create the graphics disclosed herein. For example, in some embodiments, flexography may be used. In particular, flexography may utilize printing plates made of rubber or plastic with a slightly raised image thereon. The inked plates are rotated on a cylinder which transfers the image to the sheet. Flexography may be a relatively high-speed print process that uses fast-drying inks. Other embodiments may utilize gravure printing. More particularly, gravure printing utilizes an image etched on the surface of a metal plate. The etched area is filled with ink and the plate is rotated on a cylinder that transfers the image to the sheet. In some embodiments, printing devices such as disclosed in U.S. Patent Publication No. 2012/0222576 A1 may be used.

In addition to the aforementioned various types of printing processes, it is to be appreciated that various types of inks or ink systems may be applied to various types of sheets to create the disclosed patterns, such as solvent-based, water-based, and UV-cured inks. Some embodiments may utilize inks such as Artistri® Inks available from DuPont™, including 500 Series Acid Dye Ink; 5000 Series Pigment Ink; 700 Series Acid Dye Ink; 700 Series Disperse Dye Ink; 700 Series Reactive Dye Ink; 700 Series Pigment Ink; 2500 Series Acid Dye Ink; 2500 Series Disperse Dye Ink; 2500 Series Reactive Dye Ink; 2500 Series Pigment Dye Ink; 3500 Series Disperse Dye Ink; 3500 Series Pigment Dye Ink; and Solar Brite™ Ink. Ink such as disclosed in U.S. Pat. No. 8,137,721 may also be utilized. Water-based inks that may be utilized are available from Environmental Inks and Coatings Corporation, Morganton, N.C., under the following code numbers: EH034677 (yellow); EH057960 (magenta); EH028676 (cyan); EH092391 (black); EH034676 (orange); and EH064447 (green). Some embodiments may utilized water based inks composed of food-grade ingredients and formulated to be printed directly onto ingestible food or drug products, such as Candymark Series inks available in colors such as black pro, red pro, blue pro, and yellow pro, available from Inkcups located in Danvers, Mass. Other broad ranges of general purpose and specialty inks may also be used, including food grade inks available from Videojet Technologies Inc. located in Wood Dale, Ill. Additional example inks include Collins 186-150-6 LED Cyan Ink; Collins 186-150-7 LED Magenta Ink; Collins 186-150-6 LED Yellow Ink; Collins 186-150-5 LED Black Ink; and Videojet Ink 99-51 SR.

The primary difference among the ink systems is the method used for drying or curing the ink. For example, solvent-based and water-based inks are dried by evaporation, while UV-cured inks are cured by chemical reactions. Inks may also include components, such as solvents, colorants, resins, additives, and (for ultraviolet inks only) UV-curing compounds, that are responsible for various functions. In some embodiments, a multi-stage printing system may be utilized.

In some embodiments, to improve ink rub-off resistance, ink compositions used herein may contain a wax. Such waxes may include a polyethylene wax emulsion. Addition of a wax to the ink composition may enhances rub resistance by setting up a barrier which inhibits the physical disruption of the ink film after application of the ink to the fibrous sheet. Based on weight percent solids of the total ink composition, addition ranges for the wax may be from about 0.5% solids to 10% solids. An example polyethylene wax emulsion is JONWAX 26 supplied by S.C. Johnson & Sons, Inc. of Racine, Wis.

Figure 6:
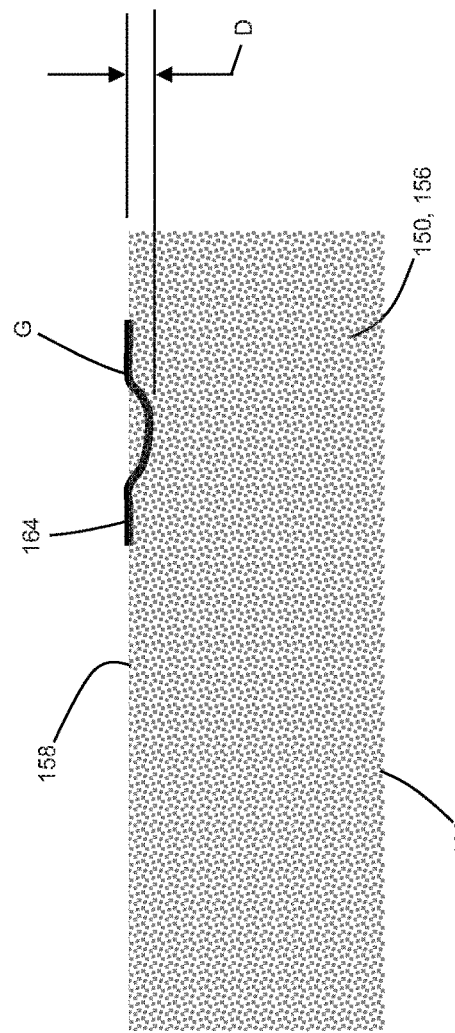
FIG. 6 illustrates a depth of ink penetration into a HIPE foam substrate.

As discussed above with reference to FIGS. 3-5, one or more graphics G may be printed directly on the first surfaces 158 and/or second surfaces 160 of HIPE foams 150 in the form of sheets 156. The graphics G include ink 164, and as such, ink may reside on the first and/or second surfaces 158, 160. In some embodiments, ink may penetrate below the first surface 158 and/or second surface 160 to various depths. For example, FIG. 6 shows a side view of a HIPE foam 150 wherein ink 164 of a printed graphic G has penetrated to an ink depth penetration, D, below the first surface 158. As such, ink 164 of a printed graphic G may reside on the HIPE foam 150 at the ink depth penetration, D, below the first and/or second surfaces 158, 160. In some embodiments, ink 164 may penetrate at an average ink depth penetration of 500 microns or less as measured with the Ink Penetration Test Method herein. In some embodiments, the average ink depth penetration may be 400 microns, 300 microns, 200 microns, 100 microns or less as measured with the Ink Penetration Test Method herein. And in some embodiments, the average ink depth penetration may be from about 50 microns to about 400 microns as measured with the Ink Penetration Test Method herein. In some embodiments, the ink depth penetration may be equal to or less than 100 microns for HIPE foams having a mean cell size of equal to or less than about 50 microns. In some embodiments, the ink depth penetration may be equal to or less than 400 microns for HIPE foams having a mean cell size from about 20 µm to about 200 µm.

While not wishing to be bound by theory, the polymeric foam structures comprising graphics printed thereon may be achieved by compounding the ink to be printed to meet select physical property ranges. For example, the print ready ink may have a surface tension so as when compared to the surface tension of the foam surfaces is lower thereby promoting the wetting of the foam cells by the print ready ink. In another example, the print ready ink may have a viscosity so upon wetting the foam cells thereby promoting ink penetration therein. In yet another example, the print ready ink may have a specific gravity so as to be relatively heavy and also promote wetting of the foam cells and thereby promoting ink penetration therein.

In some embodiments, the print ready ink composition may have a relatively low surface tension compared to the surface tension of the struts or surfaces making up the cells of the foam, so as facilitate wetting of the cells by the ink composition. The surface tension may provide desirable print ready ink wetting of the polymeric foam material. In one example, the print ready ink composition may have a surface tension as measured in dyne/cm at 25 degrees Celsius, which is numerically less than the surface tension of the struts or surfaces making up the cells of the foam. In yet another example, the print ready ink composition may have a surface tension as measured in dyne/cm at 25 degrees Celsius of less than 30.

In some embodiments, the print ready ink composition may have a viscosity such that ink penetration occurs upon wetting the foam cells. It is to be appreciated that various factors may influence ink penetration, such as for example, the print ready ink's resistance to flow, thickness, and/or viscosity. In accordance with one embodiment, the print ready ink composition may have a viscosity in the range of 1 to 30 millipascal seconds. The viscosity measurement is done according to ASTM D 2196-99 Test Method A, where a UL adaptor is utilized and the measurements are made as outlined in ASTM D 2196-99, Test Method A at 25 C and 60 rpm. Shake time and spindle selection are as indicated within the test method.

In some embodiments, it may be desired to utilize an ink having a specific gravity that also promotes wetting of the foam cells and thereby promoting ink penetration therein. An example print ready ink composition may have a specific gravity in the range of 0.830 to 1.050. The specific gravity is measured according to ASTM D 891-95 following Method A and determined at 25 C.

It is to be appreciated that the physical properties of the print ready ink may be achieved by compounding or formulating the print ready ink to meet desired ranges. For example, desired ranges for surface tension, viscosity, or specific gravity or a combination thereof in a print ready ink may be achieved by the amount of solvent or the solvent blend used in formulating the print ready ink.

Suitable solvents for the print ready ink composition may include, without limitation, alcohols, acetates, ketones, glycol ethers, aromatic hydrocarbons, aliphatic naphthas, water and combinations thereof. As an example, suitable alcohols include ethyl alcohol, isopropyl alcohol, N-propyl alcohol, and blends thereof. Suitable acetates include ethyl acetate, N-propyl acetate, N-butyl acetate, isopropyl acetate, isobutyl acetate, butyl acetate, and blends thereof. Suitable glycol ethers include ethylene glycol monopropyl ether, ethylene glycol monobutyl ether, diethylene glycol monomethyl ether, diethylene glycol monopropyl ether, propylene glycol monomethyl ether, polyproylene glycol n-propyl ether, and blends thereof.

In some embodiments, the solvent or solvent blend in the print ready ink composition may include a "slow drying" solvent. It is believed that such a solvent may influence the wicking or flow into foam cells therein upon application of the graphic thereto before the ink composition dries. As used herein, a slow drying solvent refers to a solvent having a relatively low evaporation rate relative to n-butyl acetate. Table 1 identifies the evaporation rate for various solvents normalized relative to n-butyl acetate (the evaporation rate of n-butyl acetate=1.0). Thus, a number lower than 1 identifies the solvent as having an evaporation rate that is slower than that of n-butyl acetate. Table 1 below provides evaporation rates for a selection of solvents.

TABLE 1

| | Evaporation Rate (n-Butyl Acetate = 1) |
|---|---|
| Ethyl Acetate | 7.47 |
| Isopropyl Acetate | 4.55 |
| Ethyl Alcohol | 3.30 |
| Isopropyl Alcohol | 2.83 |

TABLE 1-continued

| | Evaporation Rate (n-Butyl Acetate = 1) |
|---|---|
| n-Propyl Acetate | 2.73 |
| n-Propyl Alcohol | 1.30 |
| Water | 0.82 |
| Propylene Glycol Methyl Ether | 0.71 |
| Propylene Glycol n-Propyl Ether | 0.21 |
| Dipropylene Glycol Methyl Ether | 0.02 |
| Dipropylene Glycol n-Butyl Ether | 0.01 |
| Propolyene Glycol | 0.0053 |
| Ethylene Glycol | 0.0036 |
| Dipropylene Glycol | 0.0008 |

In some embodiments, the solvent or solvent blend making up the print ready ink may include a slow drying solvent having an evaporation rate relative to n-butyl acetate of less than 0.8, in some embodiments less than about 0.5, and in some embodiments less than about 0.25.

It is to be appreciated that the HIPE foams with graphics printed thereon may have various ink adhesion ratings. For example, it may be desirable for a HIPE foam to have a dry average ink adhesion rating of at least about 1.5 or greater, 2.0 or greater, 3.0 or greater, or 4.0 or greater as measured with the Dry Ink Adhesion Rating Test Method herein. Further, it may be desireable for a HIPE foam to have a wet average ink adhesion rating of at least about 1.5 or greater, 2.0 or greater, 3.0 or greater, or 4.0 or greater as measured with the Wet Ink Adhesion Rating Test Method herein. It is to be appreciated that a dry ink adhesion rating and/or wet ink adhesion rating of at least about 1.5 or greater is an indication of a desired level of resistance to ink rub off.

As previously mentioned, the graphics herein may include various colors. For example, in some embodiments, a graphic includes a primary color selected from the group consisting of: cyan, yellow, magenta, and black. It is also to be appreciated that the primary colors may have various optical densities. For example, in some embodiments, the primary color of cyan has an optical density of greater than about 0.1. In other embodiments, the primary color of yellow has an optical density of greater than about 0.1. In still other embodiments, the primary color of magenta has an optical density of greater than about 0.1. In yet other embodiments, the primary color of black has an optical density of greater than about 0.1.

A color's identification is determined according to the Commission Internationale de l'Eclairage L*a*b* Color Space (hereinafter "CIELab"). CIELab is a mathematical color scale based on the Commission Internationale de l'Eclairage (hereinafter "CIE") 1976 standard. CIELab allows a color to be plotted in a three-dimensional space analogous to the Cartesian xyz space. Any color may be plotted in CIELab according to the three values (L*, a*, b*). For example, there is an origin with two axis a* and b* that are coplanar and perpendicular, as well as an L-axis which is perpendicular to the a* and b* axes, and intersects those axes only at the origin. A negative a* value represents green and a positive a* value represents red. CIELab has the colors blue-violet to yellow on what is traditionally the y-axis in Cartesian xyz space. CIELab identifies this axis as the b*-axis. Negative b* values represent blue-violet and positive b* values represent yellow. CIELab has lightness on what is traditionally the z-axis in Cartesian xyz space. CIELab identifies this axis as the L-axis. The L*-axis ranges in value from 100, which is white, to 0, which is black. An L* value of 50 represents a mid-tone gray (provided that a* and b* are 0). Any color may be plotted in CIELab according to the three values (L*, a*, b*). As described herein, equal distances in CIELab space correspond to approximately uniform changes in perceived color. As a result, one of skill in the art is able to approximate perceptual differences between any two colors by treating each color as a different point in a three dimensional, Euclidian, coordinate system, and calculating the Euclidian distance between the two points ($\Delta E^*_{ab}$).

The three dimensional CIELab allows the three color components of chroma, hue, and lightness to be calculated. Within the two-dimensional space formed from the a-axis and b-axis, the components of hue and chroma can be determined. Chroma, (C*), is the relative saturation of the perceived color and can be determined by the distance from the origin in the a*b* plane. Chroma, for a particular a*, b* set can be calculated as follows:

$$C^* = (a^{*2} + b^{*2})^{1/2}$$

Figure 7:
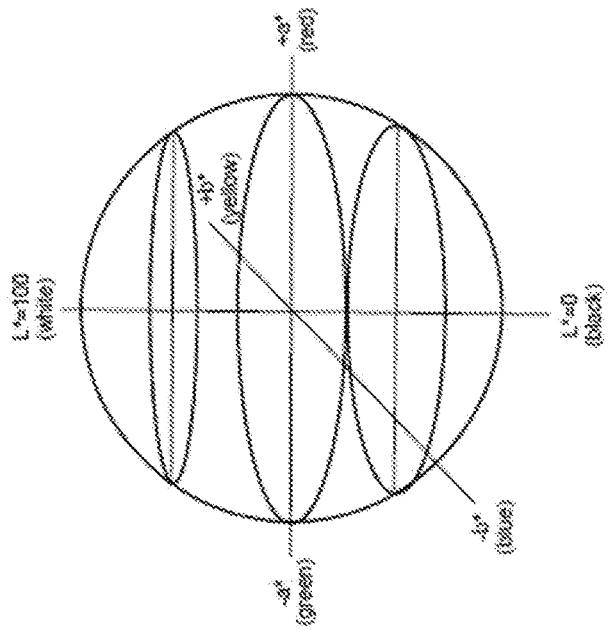
FIG. 7 is an illustration of three axes (i.e. L*, a*, and b*) used with the CIELAB color scale.

For example, a color with a*b* values of (10,0) would exhibit a lesser chroma than a color with a*b* values of (20,0). The latter color would be perceived qualitatively as being "more red" than the former. Hue is the relative red, yellow, green, and blue-violet in a particular color. A ray can be created from the origin to any color within the two-dimensional a*b* space. FIG. 7 is an illustration of three axes (respectively for the L*, a*, and b* value of a given color) used with the CIELAB color scale.

With reference to the CIELab coordinate system referred to above, a graphic printed directly on the HIPE foam structure, the graphic comprising L*a*b* color values, the graphic being defined by the CIELab coordinate values disposed inside the boundary described by the following system of equations:

{$a^*$=−5.66 to −13.27; $b^*$=59.89 to 57.29}→$b^*$=0.342$a^*$+61.824

{$a^*$=−13.27 to −25.02; $b^*$=57.29 to 40.39}→$b^*$=1.438$a^*$+76.376

{$a^*$=−25.02 to −35.25; $b^*$=40.39 to 14.23}→$b^*$=2.557$a^*$+104.371

{$a^*$=−35.25 to −35.55; $b^*$=14.23 to −0.42}→>$b^*$=48.833$a^*$+1735.605

{$a^*$=−35.55 to −16.05; $b^*$=−0.42 to −40.40}→$b^*$=−2.050$a^*$−73.307

{$a^*$=−16.05 to 5.30; $b^*$=−40.40 to −32.69}→$b^*$=0.361$a^*$−34.604

{$a^*$=5.30 to 34.81; $b^*$=−32.69 to −12.63}→$b^*$=0.680$a^*$−36.293

{$a^*$=34.81 to 39.33; $b^*$=−12.63 to −5.99}→$b^*$=1.469$a^*$−63.767

{$a^*$=39.33 to 44.16; $b^*$=−5.99 to 17.53}→$b^*$=4.870$a^*$−197.510

{$a^*$=44.16 to 42.52; $b^*$=17.53 to 33.24}→$b^*$=−9.579$a^*$+440.550

{$a^*$=42.52 to 0.92; $b^*$=33.24 to 58.23}→$b^*$=−0.601$a^*$+58.783

Figure 8A:
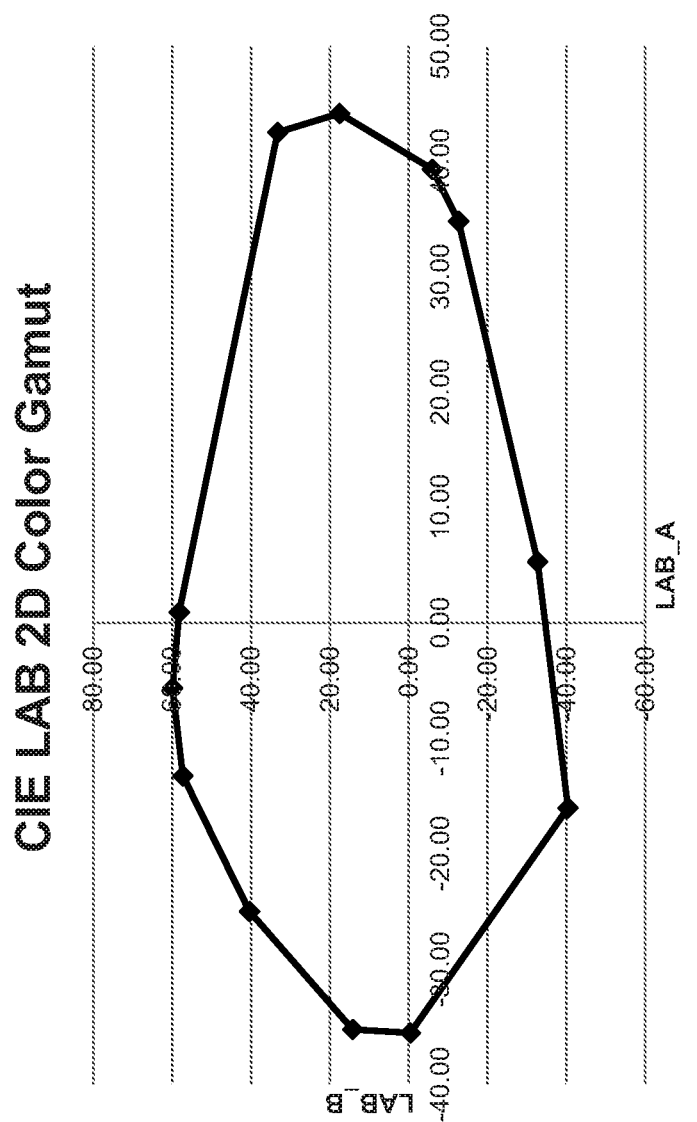
FIG. 8A is a first graphical representation of a color gamut in CIELab (L*a*b*) coordinates showing the a*b* plane where L*=0 to 100.

{$a^*$=0.92 to −5.66; $b^*$=58.23 to 59.89}→$b^*$=−0.252$a^*$+58.462; and wherein L* is from 0 to 100. FIG. 8A is a first graphical representation of the color gamut in CIELab (L*a*b*) coordinates described above showing the a*b* plane where L*=0 to 100. In some embodiments, HIPE foams having a mean cell size of equal to or less than about 50 microns may have graphics with the color gamut shown in FIG. 8A and defined by associated equations.

In another example, a graphic printed directly on the HIPE foam structure, the graphic comprising L*a*b* color values, the graphic being defined by the CIELab coordinate values disposed inside the boundary described by the following system of equations:

{$a^*$=2.35 to −20.19; $b^*$=79.81 to 70.46}→$b^*$=0.415$a^*$+78.835

{$a^*$=−20.19 to −40.21; $b^*$=70.46 to 53.48}→$b^*$=0.848$a^*$+87.584

{$a^*$=−40.21 to −51.26; $b^*$=53.48 to 20.56}→$b^*$=2.979$a^*$+173.273

{$a^*$=−51.26 to −53.16; $b^*$=20.56 to 2.64}→>$b^*$=9.432$a^*$+504.023

{$a^*$=−53.16 to −39.12; $b^*$=2.64 to −30.65}→$b^*$=−2.371$a^*$−173.407

{$a^*$=−39.12 to −24.29; $b^*$=−30.65 to −50.76}→$b^*$=−1.356$a^*$−83.698

{$a^*$=−24.29 to 5.66; $b^*$=−50.76 to −44.78}→$b^*$=0.200$a^*$−45.910

{$a^*$=5.66 to 46.22; $b^*$=−44.78 to −21.00}→$b^*$=0.586$a^*$−48.098

{$a^*$=46.22 to 52.70; $b^*$=−21.00 to −12.76}→$b^*$=1.272$a^*$−79.774

{$a^*$=52.70 to 55.98; $b^*$=−12.76 to 9.83}→$b^*$=6.887$a^*$−375.715

{$a^*$=55.98 to 43.71; $b^*$=9.83 to 47.92}→$b^*$=−3.104$a^*$+183.610

Figure 8B:
FIG. 8B is a second graphical representation of a color gamut in CIELab (L*a*b*) coordinates showing the a*b* plane where L*=0 to 100.

{$a^*$=43.71 to 2.35; $b^*$=47.92 to 79.81}→$b^*$=−0.771$a^*$+81.622; and wherein L* is from 0 to 100. FIG. 8B is a second graphical representation of the color gamut in CIELab (L*a*b*) coordinates described above showing the a*b* plane where L*=0 to 100. In some embodiments, HIPE foams having a mean cell size of equal to about 20 μm to about 200 μm may have graphics with the color gamut shown in FIG. 8B and defined by associated equations.

It is to be appreciated that the HIPE foams disclosed herein including graphics printed thereon may be used as absorbent core materials in absorbent articles, such as feminine hygiene articles, for example pads, pantiliners, and tampons; disposable diapers; incontinence articles, for example pads, adult diapers; homecare articles, for example wipes, pads, towels; and beauty care articles, for example pads, wipes, and skin care articles, such as used for pore cleaning; and wound care articles. To help provide additional context to the subsequent discussion of printing graphics on HIPE foams, the following provides a description of HIPE foams that may be printed in accordance with the present disclosure and used as components in absorbent articles.

It is to be appreciated that the homogeneous or heterogeneous polymeric foams of the present disclosure may be particularly useful as at least a portion of the absorbent structures for various absorbent articles. Use of the term "absorbent article" herein is meant a consumer product that is capable of absorbing significant quantities of urine or other fluids, such as for example, aqueous fecal matter (runny bowel movements), discharged by an incontinent wearer or user of the article. Examples of such absorbent articles include disposable diapers, incontinence garments, catamenials, such as tampons and sanitary napkins, disposable training pants, bed pads, and the like. The absorbent foam structures herein may be particularly suitable for use in articles such as diapers, incontinence pads or garments, clothing shields, and the like. It is to be appreciated that various diaper configurations may include the printed absorbent foam structures herein, such as for example, taped diapers and pant diapers.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082.

For the purposes of a specific illustration, FIG. 9 shows one example of a disposable absorbent article 250, such as described in U.S. Patent Publication No. 2008/0132865 A1, in the form of a diaper 252 that may include absorbent foam structures with printed graphics as disclosed herein. In particular, FIG. 9 is a plan view of one embodiment of a diaper 252 including a chassis 254 shown in a flat, unfolded condition, with the portion of the diaper 252 that faces a wearer oriented towards the viewer. A portion of the chassis structure is cut-away in FIG. 9 to more clearly show the construction of and various features that may be included in embodiments of the diaper.

As shown in FIG. 9, the diaper 252 includes a chassis 254 having a first ear 256, a second ear 258, a third ear 260, and a fourth ear 262. To provide a frame of reference for the present discussion, the chassis is shown with a longitudinal axis 264 and a lateral axis 266. The chassis 254 is shown as having a first waist region 268, a second waist region 270, and a crotch region 272 disposed intermediate the first and second waist regions. The periphery of the diaper is defined by a pair of longitudinally extending side edges 274, 276; a first outer edge 278 extending laterally adjacent the first waist region 268; and a second outer edge 280 extending laterally adjacent the second waist region 270. As shown in FIG. 9, the chassis 254 includes an inner, body-facing surface 282, and an outer, garment-facing surface 284. A portion of the chassis structure is cut-away in FIG. 9 to more clearly show the construction of and various features that may be included in the diaper. As shown in FIG. 9, the chassis 254 of the diaper 252 may include an outer covering layer 286 including a topsheet 288 and a backsheet 290. An absorbent assembly 292 may be disposed between a portion of the topsheet 288 and the backsheet 290. As discussed in more detail below, any one or more of the regions may be stretchable and may include an elastomeric material or laminate as described herein. As such, the diaper 252 may be configured to adapt to a specific wearer's anatomy upon application and to maintain coordination with the wearer's anatomy during wear.

The absorbent article may also include an elastic waist feature 202 shown in FIG. 9 in the form of a waist band 294 and may provide improved fit and waste containment. The elastic waist feature 202 may be configured to elastically expand and contract to dynamically fit the wearer's waist. The elastic waist feature 202 can be incorporated into the diaper in accordance with the methods discussed herein and may extend at least longitudinally outwardly from the absorbent assembly 292 and generally form at least a portion of the first and/or second outer edges 278, 280 of the diaper 252. In addition, the elastic waist feature may extend laterally to include the ears. While the elastic waist feature 202 or any constituent elements thereof may comprise one or more separate elements affixed to the diaper, the elastic waist feature may be constructed as an extension of other elements of the diaper, such as the backsheet 290, the topsheet 288, or both the backsheet and the topsheet. In addition, the elastic waist feature 202 may be disposed on the outer, garment-facing surface 284 of the chassis 254; the inner, body-facing surface 282; or between the inner and outer facing surfaces. The elastic waist feature 202 may be constructed in a number of different configurations including those described in U.S. Pat. No. 7,432,413; U.S. Patent Publication No. 2007/0142798; and U.S. Patent Publication No. 2007/0287983; all of which are hereby incorporated by reference herein.

As shown in FIG. 9, the diaper 252 may include leg cuffs 296 that may provide improved containment of liquids and other body exudates. In particular, elastic gasketing leg cuffs can provide a sealing effect around the wearer's thighs to prevent leakage. It is to be appreciated that when the diaper is worn, the leg cuffs may be placed in contact with the wearer's thighs, and the extent of that contact and contact pressure may be determined in part by the orientation of diaper on the body of the wearer. The leg cuffs 296 may be disposed in various ways on the diaper 252.

As previously mentioned, the diaper 252 may be provided in the form of a pant-type diaper and/or may be provided with a re-closable fastening system, which may include fastener elements in various locations to help secure the diaper in position on the wearer. For example, fastener elements may be located on the first and second ears and may be adapted to releasably connect with one or more corresponding fastening elements located in the second waist region. It is to be appreciated that various types of fastening elements may be used with the diaper.

As previously mentioned, the diaper 252 may include a backsheet 290. The backsheet 290 may also define a portion of the outer, garment-facing surface 284 of the chassis 254. The backsheet 290 may be impervious to fluids (e.g., menses, urine, and/or runny feces) and may be manufactured in part from a thin plastic film, although other flexible liquid impervious materials may also be used. The backsheet 290 may prevent the exudates absorbed and contained in the absorbent core from wetting articles which contact the diaper 100, such as bedsheets, pajamas and undergarments. The backsheet 290 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 290 may also be embossed and/or matte-finished to provide a more clothlike appearance. Further, the backsheet 290 may permit vapors to escape from the absorbent core (i.e., the backsheet is breathable) while still preventing exudates from passing through the backsheet 290. The size of the backsheet 290 may be dictated by the size of the absorbent assembly 292 and/or particular configuration or size of the diaper 252.

Also described above, the diaper 252 may include a topsheet 288. The topsheet 288 may also define all or part of the inner, body-facing surface 282 of the chassis 254. The topsheet 288 may be compliant, soft feeling, and non-irritating to the wearer's skin. It may be elastically stretchable in one or two directions. Further, the topsheet 288 may be liquid pervious, permitting liquids (e.g., menses, urine, and/or runny feces) to penetrate through its thickness. A topsheet 288 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 288 includes fibers, the fibers may be spunbond, carded, wet-laid, meltblown, hydroentangled, or otherwise processed as is known in the art.

Topsheets 288 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539. Topsheets may be selected from high loft nonwoven topsheets and aperture formed film topsheets. Apertured formed films may be used in topsheet embodiments as they may be pervious to body exudates and yet non-absorbent and have a reduced tendency to allow fluids to pass back through and rewet the wearer's skin. Thus, the surface of the formed film that is in contact with the body remains dry, thereby reducing body soiling and creating a more comfortable feel for the wearer. Example formed films are described in U.S. Pat. Nos. 3,929,135; 4,324,246; 4,342,314; 4,463,045; and 5,006,394. Each of these patents are incorporated herein by reference. Example microapertured formed film topsheets are disclosed in U.S. Pat. Nos. 4,609,518 and 4,629,643, which are incorporated by reference. The body surface of the formed film topsheet can be hydrophilic so as to help liquid to transfer through the topsheet faster than if the body surface was not hydrophilic so as to diminish the likelihood that fluid will flow off the topsheet rather than flowing into and being absorbed by the absorbent structure. In some embodiments, surfactant may be incorporated into the polymeric materials of the formed film topsheet. Alternatively, the body surface of the topsheet can be made hydrophilic by treating it with a surfactant such as is described in the above referenced U.S. Pat. No. 4,950,254, incorporated herein by reference.

As mentioned above, the diaper 252 may also include an absorbent assembly 292 that is joined to the chassis 254. As shown in FIG. 9, the absorbent assembly 292 may have a laterally extending front edge region in the front waist region 268 and may have a longitudinally opposing and laterally extending back edge region in the back waist region 270. The absorbent assembly may have a longitudinally extending right side edge and may have a laterally opposing and longitudinally extending left side edge. The absorbent assembly 292 may be at least partially disposed between the topsheet 288 and the backsheet 290 and may be formed in various sizes and shapes that are compatible with the diaper. The absorbent assembly 292 may additionally include one or more absorbent cores 293 or absorbent core layers. The absorbent cores 293 may comprise a homogeneous or heterogeneous foam 150 of the present disclosure. It is to be appreciated that diapers 252 comprising the absorbent foam structures 150 of the present disclosure can be made by using conventional diaper making techniques. For example, wood pulp fiber web ("airfelt"), modified cellulosic core absorbents, or superabsorbents sometimes used in conventional diapers may be replaced or supplemented with one or more foam structures of the present disclosure.

Figure 10:
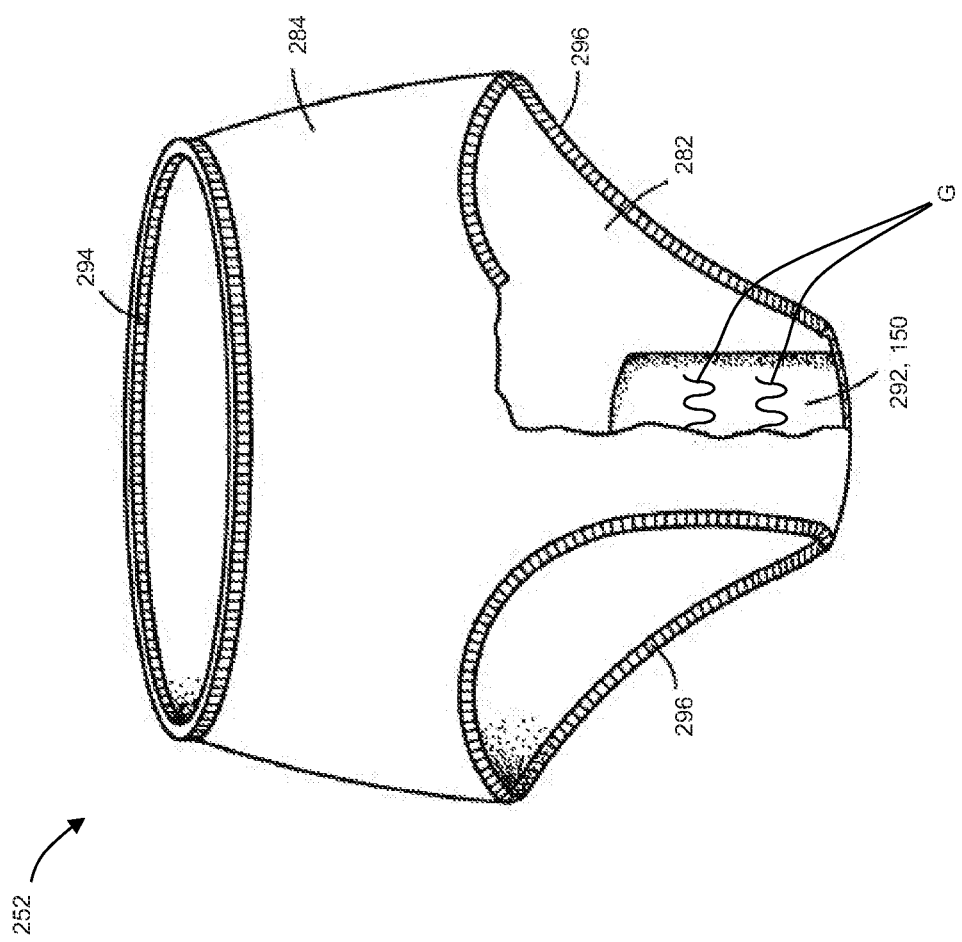
FIG. 10 is partially cut-away view of a diaper pant including an absorbent assembly having a component with graphics printed thereon.

As previously discussed, various types of diapers may be configured to include a homogeneous or heterogeneous foam 150 with graphics printed thereon. For example, the absorbent core 293 shown in FIG. 9 includes a foam structure 150 with graphics G printed thereon. As shown in FIG. 9, the graphics G are visible through the topsheet 288. FIG. 10 shows another example of a diaper 252 configured as a pant diaper including an absorbent assembly 292 including a foam structure 150 having graphics G printed thereon. The diaper 252 in FIG. 10 is partially cut away to more clearly show graphics G that are visible from the inner wearer facing surface 282 of the diaper 252.

Figure 11:
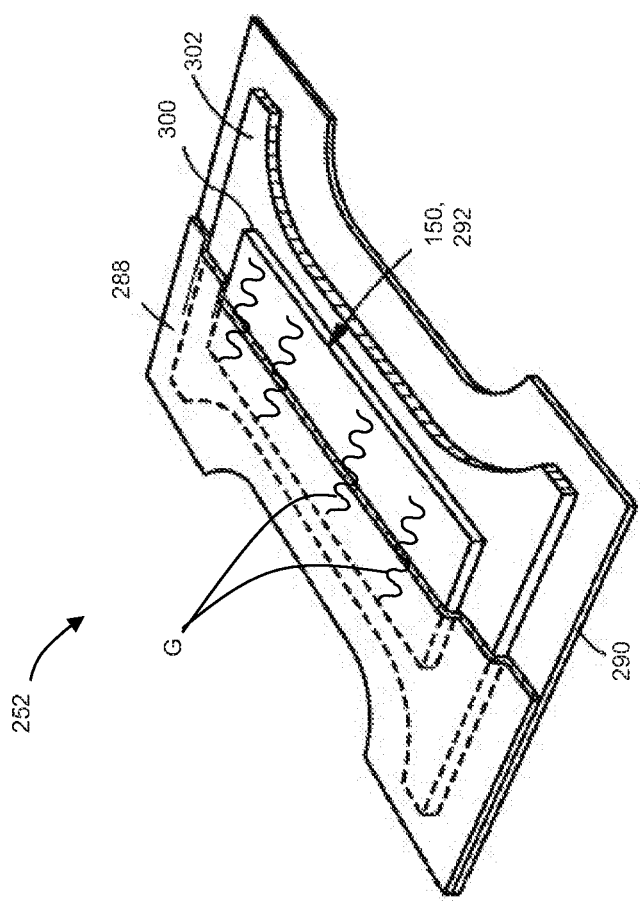
FIG. 11 is a partially cut-away view of a diaper with a multi-layered absorbent assembly having a component with graphics printed thereon.

As mentioned above, the foam structures 150 herein can be used in diapers 252 having single layer, or in various multiple layer absorbent core configurations, such as described in U.S. Pat. No. 5,387,207. For example, FIG. 11 shows a diaper 252 including an absorbent assembly 292 with multiple layers. More particularly, the absorbent assembly 292 may include an optional upper fluid acquisition layer 300, and an underlying fluid storage/redistribution layer 302 comprising an absorbent homogeneous or heterogeneous foam structure of the present disclosure. The topsheet 288 is superposed and co-extensive with one face of the absorbent assembly 292, and a backsheet 290 is superposed and coextensive with the face of the absorbent assembly opposite the face covered by the topsheet 288. The backsheet 290 may have a width greater than that of the absorbent assembly 292 thereby providing side marginal portions of the backsheet which extend beyond the absorbent assembly 292.

It is to be appreciated that a homogeneous or heterogeneous foam 150 may also be used as the acquisition layer, distribution layer, re-distribution layer, surge layer, or storage layer of an absorbent article. For example, referring back to FIG. 11, the upper acquisition layer 300 may comprise an absorbent homogeneous or heterogeneous foam structure 150 and the underlying fluid storage layer 302 may comprise a superabsorbent material. In yet another embodiment, the upper acquisition layer 300 may be configured as a fluid acquisition and distribution layer and may comprise an absorbent homogeneous or heterogeneous foam structure 150 and the underlying fluid storage layer 302 may comprise a superabsorbent material. In yet another embodiment, a diaper may comprise an absorbent assembly 292 including an intermediate distribution layer comprising an absorbent homogeneous or heterogeneous foam structure 150 positioned between the upper acquisition layer 300 and the underlying fluid storage layer 302, wherein the upper acquisition layer 300 may comprising a nonwoven and the underlying fluid storage layer 302 may comprise a superabsorbent material. In still another embodiment, the absorbent assembly 292 may include an acquisition/distribution layer 300 comprising an absorbent homogeneous or heterogeneous foam structure 150 and an underlying fluid storage layer 302 comprising a superabsorbent material particulate polymer material and a thermoplastic composition for adhering the superabsorbent material particulate polymer material to a nonwoven or film. Configurations of superabsorbent material particulate polymer material and a thermoplastic composition for adhering the superabsorbent material particulate polymer material to a nonwoven or film are described in more detail in US 2004/0167486, US 2004/0162536, US 2008/312617, and US 2012/316526, which are incorporated by reference.

It is to be appreciated that multi-layer absorbent core assemblies can also be made with homogeneous or heterogeneous polymeric foams of the present disclosure, and some configurations simplify the number of discrete layers of foam that may be used to form such multilayer composites. As discussed above with reference to FIGS. 1 and 2, a HIPE foam 150 may include a first region 152 and a second region 154 layered in the z-direction. As such, the absorbent assemblies 292 herein may be configured such that the first region 152 may be utilized as an acquisition layer 300, and the second region 154 may be utilized as a storage layer 302. In such a configuration, the first region 152 may have a relatively lower specific surface area per volume than the second region 154, which will allow the second region 154 to drain fluid from first region 152.

Figure 12:
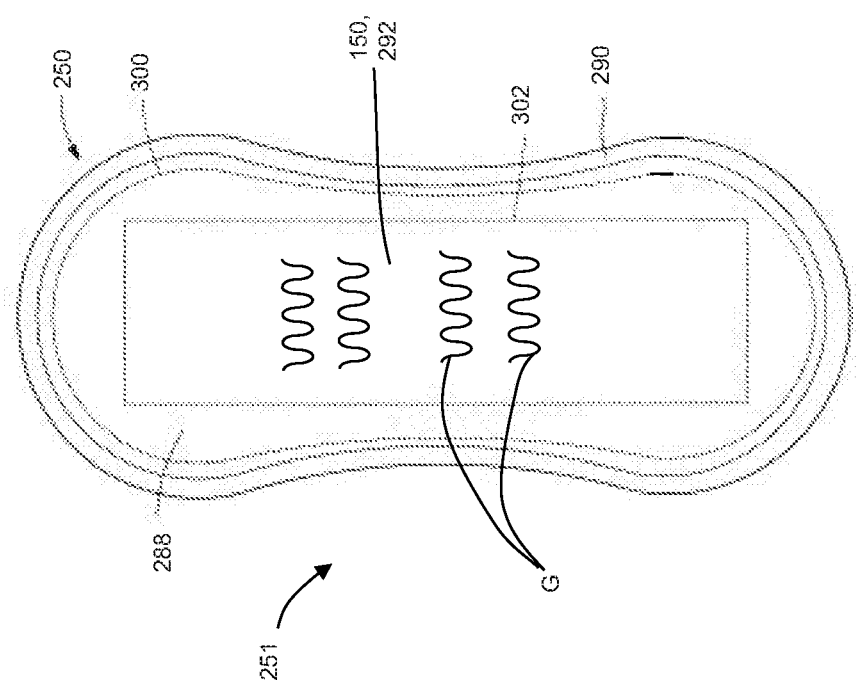
FIG. 12 shows a disposable absorbent article in the form of a catamenial pad including an absorbent assembly having a component with graphics printed thereon.

FIG. 12 shows another embodiment of an absorbent article 250 configured as catamenial pad 251 including a homogeneous or heterogeneous polymeric foam 150 of the present disclosure. The catamenial pad 251 may include fluid pervious primary topsheet 288, an absorbent core assembly 292, and a fluid impervious backsheet 290. The absorbent assembly 292 may also include an optional fluid acquisition layer 300 that may also be referred to as a secondary topsheet and a fluid storage absorbent member 302 made of one or more polymeric foams according to the present disclosure. As shown in FIG. 12, the backsheet 290 and the topsheet 288 may be positioned adjacent the garment surface and the body surface, respectively, of pad 251 and may be joined to each other. For example, the backsheet 290 and the topsheet 288 can be secured to each other by adhesive.

In use, pad 251 can be held in place by any support or attachment device known for such purposes. For example, pad 251 may be placed in the user's undergarment or panty and secured thereto by a fastener such as an adhesive. The adhesive provides a means for securing the pad in the crotch portion of the panty. Thus, a portion of or all of the outer surface of the backsheet 290 may be coated with adhesive. Various types of adhesives or glues used in the art for such purposes can be used for the adhesive herein, such as pressure-sensitive adhesives. Before pad 251 is placed in use, the pressure-sensitive adhesive may be covered with a removable release liner in order to keep the adhesive from drying out or adhering to a surface other than the crotch portion of the panty prior to use.

Other Absorbent Foams

It is to be appreciated that absorbent foams other than the HIPE foams may include graphics printed thereon as described above. For example, absorbent foams may comprise absorbent polymeric foams capable of acquiring, distributing, or storing bodily exudates fluids which have graphics printed thereon. In some embodiments, the absorbent foams may comprise a hydrophilic, flexible, nonionic polymeric foam structure of interconnected open cells which have graphics printed thereon. Embodiment may be various types of absorbent polyurethane foams or hydrophilic polyurethane foams which have graphics printed thereon.

A polyurethane foam may comprise the reaction product of at least one polyol component and a diisocyanate component. In another embodiment, a polyurethane foam may comprise the reaction product of at least one polyol component having polyethylene oxide units and a polyisocyanate component than comprises at least 25 weight % of at least one polymeric polyisocyanate than lacks urethane linkages. In some embodiments, the polyurethane foam may comprise at least 12 wt-% ethylene oxide units.

In some embodiments, the polyurethane foam may be free of superabsorbent polymer. In some embodiments, the polyurethane foam may comprise added superabsorbent polymer. In some embodiments, the polyurethane foam has a mean cell size up to 500 microns. In yet another embodiment, the polyurethane polymeric foam may have a mean cell size of at least 100 microns. In another embodiment, the polyurethane polymeric foam may have a mean cell size of at least 100 microns but less than 500 microns.

Example absorbent polymeric polyurethane foams are described in U.S. Pat. Nos. 6,852,905 and 8,980,966; and U.S. Patent Publication Nos. 2015/0080823; 2014/0295134; and 2014/0295135. Another example of absorbent polymeric polyurethane foam is described in PCT Patent Publication No. WO 2013/180937. Each of the aforementioned publications are incorporated herein by reference.

Test Methods

Unless otherwise specified, all tests described herein including those described under the Definitions section and the following test methods are conducted on samples that have been conditioned at a temperature of 23° C.±1° C. and a relative humidity of 50%±2% for a minimum of 2 hours prior to testing. All tests are conducted under the same environmental conditions. Do not test samples that have defects such as wrinkles, tears, holes, and like. Samples conditioned as described herein are considered dry samples. Further, all tests are conducted in such conditioned room.

Color and Optical Density Test Method

Background

This method provides a procedure for quantitatively measuring color and optical density of printed materials with the X-Rite SpectroEye. Optical density is a unitless value. In this method, the reflective color and optical density of a printed material is measured with the X-Rite SpectroEye, a hand held spectrophotometer, using standardized procedures and reference materials.

This method is applicable to polymeric foam structures that have been colored via printing, or other approaches directed at adding colorants to a material.

Equipment:

Hand Held Spectrophotometer: 45°/0° configuration, hemispherical geometry, X-Rite SpectroEye available from X-Rite—Corporate Headquarters USA, 4300 44th St. SE, Grand Rapids, Mich. 49512 USA, phone 616-803-2100.

White Standard Board: PG2000 available from Sun Chemical-Vivitek Division. 1701 Westinghouse Blvd., Charlotte, N.C. 28273, Phone: (704) 587-8381.

Testing Environment:

The analyses should be performed in a temperature and humidity controlled laboratory (23° C.±2° C., and 50%±2% relative humidity, respectively).

Spectrophotometer Settings:
Physical filter: None
White Base: Abs
Observer: 2°
Density Standard: ANSI T
Illumination: C NOTE: Ensure that the spectrophotometer is set to read L*a*b* units.

Procedures:
1. All samples and the White Standard Board are equilibrated at 23° C.±2° C. and 50%±2% relative humidity for at least 2 hours before analysis.
2. Select a sample region for analysis and place the sample on top of the PG2000 white standard board.
3. Place the X-Rite SpectroEye aperture over the sample and confirm that only the printed region of the sample can be viewed within the instrument aperture window.
4. Toggle through the measurement menu to read and record the color (L*, a*, and b*) and optical density values for each sample.

Calculations:
1. For each sample region, measure and record optical density readings.
2. For each optical density measurement, use three recordings to calculate and report the average and a standard deviation. Optical density values are to be reported to the nearest 0.01 units.
3. For each sample region, measure and record the color (L*, a*, and b*) readings.
4. For each color (L*, a*, b*) measurement, use three recordings to calculate and report the average of each. The L*, a*, b* values are to be reported to the nearest 0.1 units.

Dot Gain Calculation

Further to the above test method description, optical density measurements may also be used to calculate "dot gain" values. A "dot gain" is a resulting characteristic of a printing process and can be calculated using Equation 1 below:

$$\text{Dot Gain} = \frac{1 - 10(D_0 - D_N)}{1 - 10(D_0 - D_{100})} \times 100 - N \quad \text{Equation 1}$$

In Equation 1,
N is the % dot coverage;
$D_0$ is the measured optical density of a 0% dot (an unprinted substrate);
$D_{100}$ is the optical density of a 100% dot; and
$D_N$ is the optical density of a sample N % dot.

Dry Ink Adhesion Rating Test Method

This method measures the amount of color transferred from the surface of a printed polymeric foam structure to the surface of a standard woven swatch (crock-cloth), by rubbing using a rotary vertical crockmeter. Color transfer is quantified using a spectrophotometer and converted to a ink adhesion rating that ranges from 0 to 5, wherein 0=extensive transfer and 5=no transfer of color.

Equipment:
Rotary vertical crockmeter: AATCC Crockmeter, Model CM6; available from Textile Innovators Corporation, Windsor, N.C.
Standard woven swatch (crock-cloth): Model Number of the crock cloth is Shirting #3, 2 inch by 2 inch square woven swatch, available from Testfabrics Inc., West Pittston, Pa. Precision pipette, capable of delivering 0.150 mL±0.005 mL: Gilson Inc., Middleton, Wis.
Spectrophotometer, 45°/0° configuration, hemispherical geometry; HunterLab Labscan XE with Universal Software 3.80; available from Hunter Associates Laboratory Inc., Reston, Va.
Reagent: Purified water, deionized.

Instrument Set Up and Calibration:

| The Hunter Color meter settings are as follows: | |
| --- | --- |
| Geometry | 45/0 |
| Color Scale | CIE L*a*b* |
| Illumination | D65 |
| View Angle | 10° |
| Pore size | 0.7 inch |
| Illumination area | 0.5 inch |
| UV Filter | nominal |

Color is reported as L*a*b* values±0.1 units. Calibrate the instrument per instructions using the standard black and white plates provided by the vendor. Calibration should be performed each day before analyses are performed. The analyses should be performed in a temperature and humidity controlled laboratory (23° C.±2° C., and 50%±2% relative humidity, respectively).

Procedure:
1. All samples and crock-cloths are equilibrated at 23° C.±2° C. and 50%±2% relative humidity for at least 2 hours before analysis.
2. Center a single crock-cloth over the port of the color meter and cover it with the standard white plate. Take and record the reading. This is the reference L*a*b* value.
3. Mount the dry crock-cloth on to the crock meter foot.
4. Add a 64 gram weight to the vertical shaft and then lower the foot onto the sample. The actual loading on the sample is the normal instrument weight and the incremental 64 gram weight only. Securely hold the sample in place and turn the crockmeter handle five full rotations. (1 rotation=2 cycles)
5. Raise the foot and remove the crock-cloth. Avoid finger contact with the test area and rubbed region.
6. Place the crock-cloth with the test side facing the orifice of the color meter, being careful to center the rubbed region over the port. Cover it with the standard white plate. Take and record the L*a*b* reading. This is the sample value.
7. Repeat these steps 2 through 6 for each of the 3 replicates.

Calculations:

Calculate ΔE* for each replicate as follows from the set of color reference readings and the after crocking (rubbed) color readings:

$$\Delta E^* = [(L^*_{reference} - L^*_{rubbed})^2 + (a^*_{reference} - a^*_{rubbed})^2 + (b^*_{reference} - b^*_{rubbed})^2]^{1/2}$$

Convert the ΔE* value obtained to an Ink Adhesion Rating (IAR) by using the following equation:

$$IAR = -0.0001(\Delta E^*)^3 + 0.0088(\Delta E^*)^2 - 0.295\Delta E^* + 5.00$$

Reporting:

Ink Adhesion Rating values are reported as the average of 3 replicates to ±0.1 units.

Wet Ink Adhesion Rating Test Method

This method measures the amount of color transferred from the surface of a printed polymeric foam structure to the surface of a standard woven swatch (crock-cloth), by rubbing using a rotary vertical crockmeter. Color transfer is quantified using a spectrophotometer and converted to a ink adhesion rating that ranges from 0 to 5, wherein 0=extensive transfer and 5=no transfer of color.

Equipment:
Rotary vertical crockmeter: AATCC Crockmeter, Model CM6; available from Textile Innovators Corporation, Windsor, N.C.

Standard woven swatch (crock-cloth): Model Number of the crock cloth is Shirting #3, 2 inch by 2 inch square woven swatch, available from Testfabrics Inc., West Pittston, Pa. Precision pipette, capable of delivering 0.150 mL±0.005 mL: Gilson Inc., Middleton, Wis.

Spectrophotometer, 45°/0° configuration, hemispherical geometry; HunterLab Labscan XE with Universal Software 3.80; available from Hunter Associates Laboratory Inc., Reston, Va.

Reagent: Purified water, deionized.

Instrument Set Up and Calibration:

| The Hunter Color meter settings are as follows: | |
|---|---|
| Geometry | 45/0 |
| Color Scale | CIE L*a*b* |
| Illumination | D65 |
| View Angle | 10° |
| Pore size | 0.7 inch |
| Illumination area | 0.5 inch |
| UV Filter | nominal |

Color is reported as L*a*b* values±0.1 units. Calibrate the instrument per instructions using the standard black and white plates provided by the vendor. Calibration should be performed each day before analyses are performed. The analyses should be performed in a temperature and humidity controlled laboratory (23° C.±2° C., and 50%±2% relative humidity, respectively).

Procedure:
1. All samples and crock-cloths are equilibrated at 23° C.±2° C. and 50%±2% relative humidity for at least 2 hours before analysis.
2. Create reference sample by wetting a clean dry crock-cloth using 0.15 ml of the reagent. Let it dry overnight (at least 12 hours) in the 23° C.±2° C. and 50%±2% relative humidity environment.
3. After the above wetted crock-cloth has dried, center it above dry crock-cloth over the port of the color meter and cover it with the standard white plate. Take and record the L*a*b* reading. This is the reference value.
4. Mount a clean dry crock-cloth on to the crock meter foot prior wetting. Using a pipette, add 0.15 ml of the reagent to the surface of the crock-cloth, uniformly wetting the contact area.
5. Within one minute of wetting, add a 64 gram weight to the vertical shaft and then lower the foot onto the sample. The actual loading on the sample is the normal instrument weight and the incremental 64 gram weight only. Securely hold the sample in place and turn the crockmeter handle five full rotations. (1 rotation=2 cycles).
6. Raise the foot and remove the crock-cloth. Avoid finger contact with the test area and rubbed region.
7. Let the above wet rubbed crock-cloth dry before proceeding to color measurement. Let it dry overnight (at least 12 hours) in the 23° C.±2° C. and 50%±2% relative humidity environment.
8. Place the above dry crock-cloth sample with the test side facing the orifice of the color meter, being careful to center the rubbed region over the port. Cover it with the standard white plate. Take and record the L*a*b* reading. This is the sample value.
9. Repeat these steps 2 through 8 for each of the 3 replicates.

Calculations:

Calculate ΔE* for each replicate as follows from the set of color reference readings and the after crocking (rubbed) color readings:

$$\Delta E^* = [(L^*_{reference} - L^*_{rubbed})^2 + (a^*_{reference} - a^*_{rubbed})^2 + (b^*_{reference} - b^*_{rubbed})^2]^{1/2}$$

Convert the ΔE* value obtained to an Ink Adhesion Rating (IAR) by using the following equation:

$$IAR = -0.0001(\Delta E^*)^3 + 0.0088(\Delta E^*)^2 - 0.295\Delta E^* + 5.00$$

Reporting:

Ink Adhesion Rating values are reported as the average of 3 replicates to ±0.1 units.

Color Gamut Test Method

Sample Preparation:

2500 color patches (6 mm by 6 mm individual color patches) are printed on the polymeric foam structure. A CYMK ink combination is used for building and printing the color patches. The patches are printed where for each of the CYMK colors, there is a variation in the percent dot coverage from 0 to 100. For convenience of printing and measurement the color patches, the color profile can be printed in rows, columns, and in patterns as illustrated by the ANSI Color Characterization Target IT8.7/4 disclosure on page 161 of FLEXOGRAPHIC IMAGE REPRODUCTION SPECIFICATIONS & TOLERANCES (Flexographic Technical Association (FTA), Flexographic Image Reproduction Specifications & Tolerances, 900 Marconi Avenue, Ronkonkoma, N.Y. 11779-7212; www.flexography.org).

Equipment:
X-Rite iProfiler (including spectrophotometer and i1/i0 table)
X-Rite—Corporate Headquarters USA, 4300 44th St. SE, Grand Rapids, Mich. 49512 USA, phone 616-803-2100.

Spectrophotometer settings:
Physical filter: None
Observer: 2°
Illumination: D50 illuminant
Measurement geometry: 45°/0°
NOTE: Ensure that the spectrophotometer is set to read L*a*b* units.

White Standard Board: PG2000 available from Sun Chemical-Vivitek Division, 1701 Westinghouse Blvd., Charlotte, N.C. 28273, Phone: (704) 587-8381.

Measurement Procedure:
1. Set up the spectrophotometer per settings specified above.
2. Before taking color measurements, calibrate the instrument according to manufacturer instructions.
3. Printed samples are in a dry state and equilibrated at an ambient relative humidity of approximately 50%±2% and a temperature of 23° C.±1° C. for at least 2 hrs prior to analysis.
4. Place the sample to be measured on a PG2000 standard white board. Set the white board on i1i0 table.
5. Define the first and last color patch for the i1/i0 table. Set the i1/io table to start color measurement from the first color patch through the last color patch. The L*, a*, and b* values from all color patches are read and recorded.

Calculations:
1. The collected CIELAB L*, a*, b* data set is plotted in a 2-dimension space with a* and b* axes.
2. The color gamut can be approximated by drawing straight lines to between the outer-most points of the fibrous web color gamut.
3. Equations for these lines are generated by doing linear regressions to fit the straight line between the two adjacent outer-most points.

The polymeric foam structure color gamut occupies color space described by the area where the a* and b* axes of the CIELab (L*, a*, b*) color space enclosed by the system of equations described above, where L*=0 to 100.

Ink Penetration Depth Test Method

Ink Depth Penetration is measured using a Zeiss Stemi SV 11 stereomicroscope (available from Carl Zeiss Microimaging GmbH, Göttingen, Germany) equipped with a OptixCam Summit OCS-3.0 camera interfaced with OC View software version 7.3. (available from The Microscope Store, LLC, Roanoke, Va., or equivalent 3.0 MP camera and software) using reflected illumination from a halogen light source. Linear distances within the captured images are measured using Axiovision image analysis software (Carl Zeiss Microimaging GmbH, Göttingen, Germany).

Using a new Teflon coated razor blade (GEM Stainless Steel Coated, Single Edge Industrial Blades), a section about 2.5 cm in length was cut from the foam region containing the printed feature, then mounted for viewing the cross-section by carefully placing it edge down onto double sided transparent tape (e.g., Scotch Double Sided Tape 665) stuck to a standard glass microscope slide (e.g. Precleaned Gold Seal® Rite-On Microslides or equivalent). The section was mounted perpendicular to the glass slide and microscope stage with the length running parallel to the surface of the glass slide. The sample was visually checked and adjusted, if necessary, to minimize tilting to any angle. The magnification selected was 4.8× using a Zeiss 1× Plan S objective with a 0.6× C-mount camera adaptor and 0.8× zoom.

Once the cross-section plane of the sample was brought into view and approximate focus with an optimal camera exposure time, an image was collected using the OC View software. Two non-overlapping images per sample were collected. Sample images were loaded into Axiovision software and each image was spatially calibrated against and ANSI certified ruler divided into millimeter increments captured in the same manner as the sample images. Spatial calibration is used to establish pixel size and allow for conversion to standard units.

The distance of ink penetration into the foam is measured, beginning from the top surface over which the ink is deposited to the point perpendicular to that surface at which ink can no longer be observed. The top surface is defined as the upper most exposed region which can be physically addressed with human hand or tool and is readily visible by the human eye. Thus the top surface is taken as the local surface specific to the ink printed point of interest on the sample. Ten measurements of ink depth penetration were made on each of the two images, wherein the measurements span the image width. As such, a total of twenty measurements are obtained per sample with all recorded to the nearest micron. An average of the twenty measurements is calculated for each sample and reported along with the median and maximum value to the nearest micron.

Method for Measuring Mean Cell Size

The foam sample to be analyzed is cut into 1 cm wide strips using a single edge PTFE-treated razor blade such as GEM® razor blades available from Ted Pella Inc. For each new set of samples, a new razor blade is used so as to generate a clean cross section of each foam sample. This cross section will be subject of the cell size measurements. Cut samples are placed in a glass fritted filter/funnel and washed with distilled water and then isopropanol. The washing cycle is repeated two more times for a total of six washings. The samples are then dried for 24 hours at room temperature. Cross sections of these samples are made viewable by adhering to a Scanning Electron Microscope (SEM) mount using double-side copper (Cu) tape, sputter gold (Au) coated, and then placed in the SEM for images acquisition. Most commercially available SEMs can provide the images required. One such SEM is the Hitachi S-4700 with PCI (Passive Capture Imaging) software for image analysis or an equivalent SEM system and equivalent software.

SEM images are acquired at a magnification where measurements are possible along an imaginary line traversing the foam distinct region being measured. Cell diameters are measured by manually drawing a line across the diameter of a cell in a calibrated SEM image, using image analysis software such as Image Pro Plus v7.0 or equivalent software. All cells in an image are measured. Individual cell diameter measurements are collected in a spreadsheet where the mean cell size is calculated. There are typically at least 150 cells counted for each sample. For a given sample, the mean cell size measurement is reported in microns.

Examples of Printed Polymeric Foam Structures for Optical Density Measurements

Sheet of Polymeric Foam Structure and Print Conditions

A sheet of polymeric foam structure was cut from a roll of polymeric foam structure as described above. The sheet of polymeric foam structure was then secured on a platen of an Konica Minolta XY200 inkjet printing system with a KM1024i print head with a printing gap (distance between nozzle plate and surface of the sheet of web) set to 2 mm. The resolution was set at 360 dpi×360 dpi, wherein 360 dpi was the resolution in a machine direction and 360 dpi was the resolution in a cross direction. The print line velocity was 400 mm/s and the print head temperature was 45° C. The droplet size was set to 14 picoliters. The printed ink was cured with an off-line LED (light emitting diode) lamp at 53 feet/min having operating at 8 watts/cm$^2$ and a wavelength of 395 nm.

A tonal chart for cyan, magenta, yellow, and black colors were printed on separate sheets of polymeric foam structure, wherein each tonal chart comprises 11 color patches with the following % dot coverage: 0%, 10%, 20%, 30%, 40%, 50%, 60%, 70%, 80%, 90%, and 100%.

1. CYAN Color Examples

Example 1 Polymeric Foam Structure—Cyan

A tonal chart for cyan color was printed on a region of a sheet of polymeric foam structure with Collins 186-150-6 LED Cyan Ink, wherein the mean cell size of the region was 11 μm.

Example 2 Polymeric Foam Structure Cyan

A tonal chart for cyan color was printed on a region of a sheet of polymeric foam structure with Collins 186-150-6 LED Cyan Ink, wherein the mean cell size of the region was 55 μm.

2. MAGENTA Color Example

Example 1 Polymeric Foam Structure—Magenta

A tonal chart for cyan color was printed on a region of a sheet of polymeric foam structure with Collins 186-150-7 LED Magenta Ink, wherein the mean cell size of the region was 11 μm.

Example 2 Polymeric Foam Structure Magenta

A tonal chart for cyan color was printed on a region of a sheet of polymeric foam structure with Collins 186-150-7 LED Magenta Ink, wherein the mean cell size of the region was 55 μm.

3. YELLOW Color Example

Example 1 Polymeric Foam Structure—Yellow

A tonal chart for cyan color was printed on a region of a sheet of polymeric foam structure with Collins 186-150-6 LED Yellow Ink, wherein the mean cell size of the region was 11 μm.

Example 2 Polymeric Foam Structure Yellow

A tonal chart for cyan color was printed on a region of a sheet of polymeric foam structure with Collins 186-150-8 LED Yellow Ink, wherein the mean cell size of the region was 55 μm.

4. BLACK Color Example

Example 1 Polymeric Foam Structure—Black

A tonal chart for cyan color was printed on a region of a sheet of polymeric foam structure with Collins 186-150-5 LED Black Ink, wherein the mean cell size of the region was 11 μm.

Example 2 Polymeric Foam Structure Black

A tonal chart for cyan color was printed on a region of a sheet of polymeric foam structure with Collins 186-150-5 LED Black Ink, wherein the mean cell size of the region was 55 μm.

Optical density of each sheet was measured and recorded in accordance with the Color and Optical Density Test Method herein.

The recorded "optical density vs. % dot coverage" data for each color example are presented in Tables 2A and 2C below, and the associated "dot gain" values for each color example are presented in Tables 2B and 2D below.

TABLE 2A

Example 1 Polymeric Foam Structure with Mean Cell Size of 11 μm

| Dot Coverage (%) | Optical Density | | | |
|---|---|---|---|---|
| | Cyan | Magenta | Yellow | Black |
| 0 | 0.09 | 0.08 | 0.08 | 0.08 |
| 10 | 0.20 | 0.13 | 0.12 | 0.19 |
| 20 | 0.30 | 0.18 | 0.19 | 0.30 |
| 30 | 0.39 | 0.23 | 0.25 | 0.43 |
| 40 | 0.46 | 0.29 | 0.30 | 0.55 |
| 50 | 0.56 | 0.35 | 0.35 | 0.63 |
| 60 | 0.69 | 0.40 | 0.41 | 0.74 |
| 70 | 0.92 | 0.48 | 0.45 | 0.82 |
| 80 | 0.99 | 0.60 | 0.49 | 0.84 |
| 90 | 1.05 | 0.66 | 0.58 | 0.95 |
| 100 | 1.16 | 0.85 | 0.62 | 0.98 |

TABLE 2B

Example 1 Summary of Associated Dot Gain Information For Polymeric Foam Structure with Mean Cell Size of 11 μm

| Dot Coverage (%) | Associated Dot Gain Calculation | | | |
|---|---|---|---|---|
| | Cyan | Magenta | Yellow | Black |
| 0 | 0.0 | 0.0 | 0.0 | 0.0 |
| 10 | 14.7 | 3.1 | 3.4 | 15.5 |
| 20 | 21.8 | 4.5 | 11.3 | 25.5 |
| 30 | 24.9 | 6.6 | 15.9 | 32.3 |
| 40 | 23.3 | 6.4 | 15.7 | 35.1 |
| 50 | 22.8 | 6.1 | 14.5 | 32.1 |
| 60 | 22.1 | 2.8 | 14.3 | 29.4 |
| 70 | 23.2 | 2.5 | 10.8 | 23.6 |
| 80 | 15.4 | 3.9 | 5.8 | 14.4 |
| 90 | 7.2 | −2.7 | 5.9 | 8.8 |
| 100 | 0.0 | 0.0 | 0.0 | 0.0 |

TABLE 2C

Example 2 Polymeric Foam Structure with Mean Cell Size of 55 μm

| Dot Coverage (%) | Optical Density | | | |
|---|---|---|---|---|
| | Cyan | Magenta | Yellow | Black |
| 0 | 0.05 | 0.05 | 0.06 | 0.07 |
| 10 | 0.12 | 0.11 | 0.11 | 0.12 |
| 20 | 0.19 | 0.16 | 0.16 | 0.20 |
| 30 | 0.27 | 0.21 | 0.20 | 0.27 |
| 40 | 0.32 | 0.26 | 0.24 | 0.32 |
| 50 | 0.38 | 0.31 | 0.27 | 0.36 |
| 60 | 0.44 | 0.36 | 0.31 | 0.46 |
| 70 | 0.60 | 0.44 | 0.35 | 0.54 |
| 80 | 0.67 | 0.56 | 0.41 | 0.54 |
| 90 | 0.75 | 0.66 | 0.45 | 0.59 |
| 100 | 0.80 | 0.69 | 0.61 | 0.72 |

TABLE 2D

Example 2 Summary of Associated Dot Gain Information For Polymeric Foam Structure with Mean Cell Size of 55 μm

| Dot Coverage (%) | Associated Dot Gain Calculation | | | |
|---|---|---|---|---|
| | Cyan | Magenta | Yellow | Black |
| 0 | 0.0 | 0.0 | 0.0 | 0.0 |
| 10 | 8.2 | 5.5 | 4.5 | 4.7 |
| 20 | 13.9 | 8.3 | 7.9 | 12.4 |
| 30 | 18.2 | 9.8 | 7.5 | 16.8 |
| 40 | 16.9 | 9.4 | 6.9 | 15.7 |
| 50 | 14.7 | 7.5 | 3.4 | 13.6 |
| 60 | 11.8 | 5.0 | 0.8 | 16.2 |
| 70 | 17.2 | 6.3 | −2.1 | 14.9 |
| 80 | 12.2 | 9.4 | −2.1 | 5.3 |
| 90 | 7.6 | 8.1 | −7.2 | −0.3 |
| 100 | 0.0 | 0.0 | 0.0 | 0.0 |

Examples of Printed Polymeric Foam Structures for Wet and Dry Ink Adhesion Measurements Sheet of Polymeric Foam Structure and Print Conditions A sheet of polymeric foam structure was cut from a roll of polymeric foam structure as described above. The sheet of polymeric foam structure was then secured on a platen of a Konica Minolta XY200 inkjet printing system with a KM1024i print head with a printing gap (distance between nozzle plate and surface of the sheet of web) set to 2 mm. The resolution was set at 360 dpi×360 dpi, wherein 360 dpi was the resolution in a machine direction and 360 dpi was the resolution in a cross direction. The print line velocity was 400 mm/s and the print head temperature was 45° C. The droplet size was set to 14 picoliters. The printed ink was cured with an off-line LED (light emitting diode) lamp at 53 feet/min having operating at 8 watts/cm² and a wavelength of 395 nm. Note that the violet ink is a solvent based ink and UV curing was not required.

Example 3 Polymeric Foam Structure—Cyan

A first 2 inch by 2 inch area of the sheet was printed with cyan color, Collins 186-150-6 LED Cyan Ink, wherein the mean cell size of the region was 11 μm Example 4 Polymeric Foam Structure Cyan A first 2 inch by 2 inch area of the sheet was printed with cyan color, Collins 186-150-6 LED Cyan Ink, wherein the mean cell size of the region was 55 μm.

Example 3 Polymeric Foam Structure—Magenta

A second 2 inch by 2 inch area of the sheet was printed with magenta color, Collins 186-150-7 LED Magenta Ink, wherein the mean cell size of the region was 11 μm.

Example 4 Polymeric Foam Structure Magenta

A second 2 inch by 2 inch area of the sheet was printed with magenta color, Collins 186-150-7 LED Magenta Ink, wherein the mean cell size of the region was 55 μm.

Example 3 Polymeric Foam Structure—Yellow

A third 2 inch by 2 inch area of the sheet was printed with yellow color, Collins 186-150-6 LED Yellow Ink, wherein the mean cell size of the region was 11 μm.

Example 4 Polymeric Foam Structure Yellow

A third 2 inch by 2 inch area of the sheet was printed with yellow color, Collins 186-150-6 LED Yellow Ink, wherein the mean cell size of the region was 55 μm.

Example 3 Polymeric Foam Structure—Black

A fourth 2 inch by 2 inch area of the sheet was printed with black color, Collins 186-150-5 LED Black Ink, wherein the mean cell size of the region was 11 μm.

Example 4 Polymeric Foam Structure Black

A fourth 2 inch by 2 inch area of the sheet was printed with black color, Collins 186-150-5 LED Black Ink, wherein the mean cell size of the region was 55 μm.

Example 3 Polymeric Foam Structure—Violet

A fifth 2 inch by 2 inch area of the sheet was printed with violet color, Videojet Ink 99-51 SR, wherein the mean cell size of the region was 11 μm.

Example 4 Polymeric Foam Structure Violet

A fifth 2 inch by 2 inch area of the sheet was printed with violet color, Videojet Ink 99-51SR, wherein the mean cell size of the region was 55 μm.

Wet and dry ink adhesion ratings were measured and recorded in accordance with the Wet and Dry Adhesion Rating Test Methods herein. Each measurement was performed on an untested area of the printed sheet.

The recorded wet and dry adhesion rating data are presented in Table 3 below.

TABLE 3

Summary of Ink Adhesion Ratings

| Color | Example 3 Polymeric Foam Structure with Mean Cell Size of 11 μm | | Example 4 Polymeric Foam Structure with Mean Cell Size of 55 μm | |
|---|---|---|---|---|
| | Dry | Wet | Dry | Wet |
| Cyan | 2.12 | 3.36 | 1.97 | 1.75 |
| Magenta | 1.89 | 3.45 | 1.58 | 1.70 |
| Yellow | 1.45 | 3.11 | 1.92 | 1.71 |
| Black | 2.69 | 3.55 | 2.1 | 1.94 |
| Violet | 1.99 | 3.07 | 2.69 | 2.34 |

Examples of Printed Polymeric Foam Structures with Color Gamut Measurements

Sheet of Polymeric Foam Structure and Print Conditions

A sheet of polymeric foam structure was cut from a roll of polymeric foam structure as described above. The sheet of polymeric foam structure was then secured on a platen of a Konica Minolta XY200 inkjet printing system with a KM1024i print head with a printing gap (distance between nozzle plate and surface of the sheet of web) set to 2 mm. The resolution was set at 360 dpi×360 dpi, wherein 360 dpi was the resolution in a machine direction and 360 dpi was the resolution in a cross direction. The print line velocity was 400 mm/s and the print head temperature was 45° C. The droplet size was set to 14 picoliters. The printed ink was cured with an off-line LED (light emitting diode) lamp at 53 feet/min having operating at 8 watts/cm² and a wavelength of 395 nm.

2500 color patches (6 mm by 6 mm individual color patches) were printed on a first sheet of the polymeric foam structure wherein the mean cell size of the region was 11 µm and were printed on a second sheet of the polymeric foam structure wherein the mean cell size of the region was 55 µm. The printing was performed with Collins 186-150-6 LED Cyan Ink; Collins 186-150-7 LED Magenta Ink; Collins 186-150-6 LED Yellow Ink; and Collins 186-150-5 LED Black Ink.

The resulting color gamut was measured on the first sheet of the polymeric foam structure according to the Color Gamut Test Method and defined by the CIELab coordinate values disposed inside the boundary described by the following system of equations:

$\{a^*=-5.66 \text{ to } -13.27; b^*=59.89 \text{ to } 57.29\} \rightarrow b^*=0.342a^*+61.824$ $\{a^*=-13.27 \text{ to } -25.02; b^*=57.29 \text{ to } 40.39\} \rightarrow b^*=1.438a^*+76.376$ $\{a^*=-25.02 \text{ to } -35.25; b^*=40.39 \text{ to } 14.23\} \rightarrow b^*=2.557a^*+104.371$ $\{a^*=-35.25 \text{ to } -35.55; b^*=14.23 \text{ to } -0.42\} \rightarrow b^*=48.833a^*+1735.605$ $\{a^*=-35.55 \text{ to } -16.05; b^*=-0.42 \text{ to } -40.40\} \rightarrow b^*=-2.050a^*-73.307$ $\{a^*=-16.05 \text{ to } 5.30; b^*=-40.40 \text{ to } -32.69\} \rightarrow b^*=0.361a^*-34.604$ $\{a^*=5.30 \text{ to } 34.81; b^*=-32.69 \text{ to } -12.63\} \rightarrow b^*=0.680a^*-36.293$ $\{a^*=34.81 \text{ to } 39.33; b^*=-12.63 \text{ to } -5.99\} \rightarrow b^*=1.469a^*-63.767$ $\{a^*=39.33 \text{ to } 44.16; b^*=-5.99 \text{ to } 17.53\} \rightarrow b^*=4.870a^*-197.510$ $\{a^*=44.16 \text{ to } 42.52; b^*=17.53 \text{ to } 33.24\} \rightarrow b^*=-9.579a^*+440.550$ $\{a^*=42.52 \text{ to } 0.92; b^*=33.24 \text{ to } 58.23\} \rightarrow b^*=-0.601a^*+58.783$ $\{a^*=0.92 \text{ to } -5.66; b^*=58.23 \text{ to } 59.89\} \rightarrow b^*=-0.252a^*+58.462;$ and wherein L* is from 0 to 100. FIG. 8A is a graphical representation of the color gamut in CIELab (L*a*b*) coordinates described above showing the a*b* plane where L*=0 to 100.

The resulting color gamut was measured on the second sheet of the polymeric foam structure according to the Color Gamut Test Method and defined by the CIELab coordinate values disposed inside the boundary described by the following system of equations:

$\{a^*=2.35 \text{ to } -20.19; b^*=79.81 \text{ to } 70.46\} \rightarrow b^*=0.415a^*+78.835$ $\{a^*=-20.19 \text{ to } -40.21; b^*=70.46 \text{ to } 53.48\} \rightarrow b^*=0.848a^*+87.584$ $\{a^*=-40.21 \text{ to } -51.26; b^*=53.48 \text{ to } 20.56\} \rightarrow b^*=2.979a^*+173.273$ $\{a^*=-51.26 \text{ to } -53.16; b^*=20.56 \text{ to } 2.64\} \rightarrow b^*=9.432a^*+504.023$ $\{a^*=-53.16 \text{ to } -39.12; b^*=2.64 \text{ to } -30.65\} \rightarrow b^*=-2.371a^*-173.407$ $\{a^*=-39.12 \text{ to } -24.29; b^*=-30.65 \text{ to } -50.76\} \rightarrow b^*=-1.356a^*-83.698$ $\{a^*=-24.29 \text{ to } 5.66; b^*=-50.76 \text{ to } -44.78\} \rightarrow b^*=0.200a^*-45.910$ $\{a^*=5.66 \text{ to } 46.22; b^*=-44.78 \text{ to } -21.00\} \rightarrow b^*=0.586a^*-48.098$ $\{a^*=46.22 \text{ to } 52.70; b^*=-21.00 \text{ to } -12.76\} \rightarrow b^*=1.272a^*-79.774$ $\{a^*=52.70 \text{ to } 55.98; b^*=-12.76 \text{ to } 9.83\} \rightarrow b^*=6.887a^*-375.715$ $\{a^*=55.98 \text{ to } 43.71; b^*=9.83 \text{ to } 47.92\} \rightarrow b^*=-3.104a^*+183.610$ $\{a^*=43.71 \text{ to } 2.35; b^*=47.92 \text{ to } 79.81\} \rightarrow b^*=-0.771a^*+81.622;$ and wherein L* is from 0 to 100. FIG. 8B is a graphical representation of the color gamut in CIELab (L*a*b*) coordinates described above showing the a*b* plane where L*=0 to 100.

Examples of Printed Polymeric Foam Structures for Ink Penetration Measurements

Ink depth penetration distances were measured and recorded in accordance with the Ink Penetration Test Methods on Examples 3 and 4 are herein as presented in Table 4 below.

Example 3 Polymeric Foam Structure—Cyan

A first 2 inch by 2 inch area of the sheet was printed with cyan color, Collins 186-150-6 LED Cyan Ink, wherein the mean cell size of the region was 11 µm.

Example 4 Polymeric Foam Structure Cyan

A first 2 inch by 2 inch area of the sheet was printed with cyan color, Collins 186-150-6 LED Cyan Ink, wherein the mean cell size of the region was 55 µm.

Example 3 Polymeric Foam Structure—Magenta

A second 2 inch by 2 inch area of the sheet was printed with magenta color, Collins 186-150-7 LED Magenta Ink, wherein the mean cell size of the region was 11 µm.

Example 4 Polymeric Foam Structure Magenta

A second 2 inch by 2 inch area of the sheet was printed with magenta color, Collins 186-150-7 LED Magenta Ink, wherein the mean cell size of the region was 55 µm.

Example 3 Polymeric Foam Structure—Yellow

A third 2 inch by 2 inch area of the sheet was printed with yellow color, Collins 186-150-6 LED Yellow Ink, wherein the mean cell size of the region was 11 µm.

Example 4 Polymeric Foam Structure Yellow

A third 2 inch by 2 inch area of the sheet was printed with yellow color, Collins 186-150-6 LED Yellow Ink, wherein the mean cell size of the region was 55 µm.

Example 3 Polymeric Foam Structure—Black

A fourth 2 inch by 2 inch area of the sheet was printed with black color, Collins 186-150-5 LED Black Ink, wherein the mean cell size of the region was 11 µm.

Example 4 Polymeric Foam Structure Black

A fourth 2 inch by 2 inch area of the sheet was printed with black color, Collins 186-150-5 LED Black Ink, wherein the mean cell size of the region was 55 µm.

Example 3 Polymeric Foam Structure—Violet

A fifth 2 inch by 2 inch area of the sheet was printed with violet color, Videojet Ink 99-51SR, wherein the mean cell size of the region was 11 µm.

Example 4 Polymeric Foam Structure Violet

A fifth 2 inch by 2 inch area of the sheet was printed with violet color, Videojet Ink 99-51 SR, wherein the mean cell size of the region was 55 µm.

Example 5 Tegaderm Foam—Magenta

A second 2 inch by 2 inch area of the Tegaderm Foam was printed with magenta color, Collins 186-150-7 LED Magenta Ink.

Example 5 Tegaderm Foam—Yellow

A third 2 inch by 2 inch area of the Tegaderm Foam was printed with yellow color, Collins 186-150-6 LED Yellow Ink.

Example 5 Tegaderm Foam—Black

A fourth 2 inch by 2 inch area of the Tegaderm Foam was printed with black color, Collins 186-150-5 LED Black Ink.

Wet and dry adhesion ratings were measured and recorded for the Tegaderm Foam printed samples in accordance with the Wet and Dry Adhesion Rating Test Methods herein. Each measurement was performed on an untested area of the printed sheet. Additionally, ink depth penetration distances were measured and recorded for the Tegaderm Foam printed

TABLE 4

Summary Of Ink Depth Penetration Data

| | Example 3 | | | Example 4 | | |
| --- | --- | --- | --- | --- | --- | --- |
| Color | Average Ink Depth Penetration µm | Median Ink Depth Penetration µm | Maximum Ink Depth Penetration µm | Average Ink Depth Penetration µm | Median Ink Depth Penetration µm | Maximum Ink Depth Penetration µm |
| Magenta | 59 | 60 | 80 | 263 | 220 | 650 |
| Black | 96 | 105 | 130 | 229 | 200 | 650 |
| Cyan | 84 | 80 | 130 | 305 | 210 | 1340 |
| Yellow | 79 | 80 | 110 | 376 | 210 | 1130 |
| Violet | 76 | 70 | 100 | 310 | 315 | 520 |

Examples of Printed Polymeric Polyurethane Foam for Wet and Dry Ink Adhesion Ratings and Ink Depth Penetration Measurements Sheet of Polymeric Polyurethane Foam Structure and Print Conditions A sheet of polymeric polyurethane foam obtained from the 3M Company's 3M Health Care business which is available commercially under the name Tegaderm Foam. The sheet of Tegaderm Foam was secured on a platen of a Konica Minolta XY200 inkjet printing system with a KM1024i print head with a printing gap (distance between nozzle plate and surface of the sheet of foam) set to 2 mm. The resolution was set at 360 dpi×360 dpi, wherein 360 dpi was the resolution in a machine direction and 360 dpi was the resolution in a cross direction. The print line velocity was 400 mm/s and the print head temperature was 45° C. The droplet size was set to 14 picoliters. The printed ink was cured with an off-line LED (light emitting diode) lamp at 53 feet/min having operating at 8 watts/cm$^2$ and a wavelength of 395 nm.

Example 5 Tegaderm Foam—Cyan

A first 2 inch by 2 inch area of the Tegaderm Foam was printed with cyan color, Collins 186-150-6 LED Cyan Ink.

samples in accordance with the Ink Penetration Test Methods herein. The recorded wet and dry adhesion rating data and the ink depth penetration data are presented in Table 5 below.

TABLE 5

Summary of Ink Adhesion Ratings And Ink Depth Penetration Data For Printed Tegaderm Foam

| | Ink Adhesion Ratings | | Average Ink Depth Penetration |
| --- | --- | --- | --- |
| Color | Dry | Wet | µm |
| Cyan | 4.91 | 4.64 | 528 |
| Magenta | 4.85 | 4.50 | 469 |
| Yellow | 4.88 | 4.63 | 383 |
| Black | 4.86 | 4.60 | 378 |

Examples of Printed Polymeric Polyurethane Foam for Optical Density Measurements Sheet of Polymeric Polyurethane Foam Structure and Print Conditions A sheet of polymeric polyurethane foam obtained from the 3M Company's 3M Health Care business which is available commercially under the name Tegaderm Foam. The sheet of Tegaderm Foam was then secured on a platen of a Konica Minolta XY200 inkjet printing system with a KM1024i print head with a printing gap (distance between nozzle plate and surface of the sheet of foam) set to 2 mm. The resolution was set at 360 dpi×360 dpi, wherein 360 dpi was the resolution in a machine direction and 360 dpi was the resolution in a cross direction. The print line velocity was 400 mm/s and the print head temperature was 45° C. The droplet size was set to 14 picoliters. The printed ink was cured with an off-line LED (light emitting diode) lamp at 53 feet/min having operating at 8 watts/cm² and a wavelength of 395 nm.

A tonal chart for cyan, magenta, yellow, and black colors were printed on separate sheets of the Tegaderm Foam, wherein each tonal chart comprises 11 color patches with the following % dot coverage: 0%, 10%, 20%, 30%, 40%, 50%, 60%, 70%, 80%, 90%, and 100%.

5. CYAN Color Examples

Example 6 Tegaderm Foam—Cyan

A tonal chart for cyan color was printed on a region of the Tegaderm Foam with Collins 186-150-6 LED Cyan Ink.

6. MAGENTA Color Examples

Example 6 Tegaderm Foam—Magenta

A tonal chart for cyan color was printed on a region of the Tegaderm Foam with Collins 186-150-7 LED Magenta Ink.

7. YELLOW Color Examples

Example 6 Tegaderm Foam—Yellow

A tonal chart for cyan color was printed on a region of the Tegaderm with Collins 186-150-6 LED Yellow Ink.

8. BLACK Color Example

Example 6 Tegaderm Foam—Black

A tonal chart for cyan color was printed on a region of the Tegaderm Foam with Collins 186-150-5 LED Black Ink. Optical density of each sheet was measured and recorded in accordance with the Color and Optical Density Test Method herein. The recorded "optical density vs. % dot coverage" data for each color example are presented in Table 6 below and associated Dot Gain values are provided in Table 7.

TABLE 6

Summary of Optical Density Data For Printed Tegaderm Foam

| Dot Coverage | Optical Density | | | |
|---|---|---|---|---|
| (%) | Cyan | Magenta | Yellow | Black |
| 0 | 0.28 | 0.29 | 0.29 | 0.29 |
| 10 | 0.27 | 0.31 | 0.37 | 0.39 |
| 20 | 0.43 | 0.36 | 0.45 | 0.51 |
| 30 | 0.52 | 0.40 | 0.52 | 0.62 |
| 40 | 0.61 | 0.47 | 0.57 | 0.69 |
| 50 | 0.68 | 0.48 | 0.61 | 0.77 |
| 60 | 0.74 | 0.53 | 0.67 | 0.88 |
| 70 | 0.96 | 0.62 | 0.74 | 1.08 |
| 80 | 1.06 | 0.77 | 0.82 | 1.17 |
| 90 | 1.13 | 0.81 | 0.86 | 1.21 |
| 100 | 1.25 | 0.95 | 1.06 | 1.24 |

TABLE 7

Summary of Associated Dot Gain Information For Printed Tegaderm Foam

| Dot Coverage | Associated Dot Gain Calculation | | | |
|---|---|---|---|---|
| (%) | Cyan | Magenta | Yellow | Black |
| 0 | 0.0 | 0.0 | 0.0 | 0.0 |
| 10 | −11.3 | −5.6 | 10.4 | 11.8 |
| 20 | 12.8 | −0.8 | 16.6 | 23.6 |
| 30 | 18.3 | −1.7 | 19.0 | 29.2 |
| 40 | 20.4 | 2.4 | 17.4 | 27.3 |
| 50 | 18.0 | −4.1 | 12.5 | 25.6 |
| 60 | 13.7 | −6.3 | 10.1 | 23.7 |
| 70 | 18.5 | −1.8 | 7.4 | 24.4 |
| 80 | 13.5 | 4.9 | 5.3 | 17.8 |
| 90 | 6.1 | −0.5 | −2.0 | 9.0 |
| 100 | 0.0 | 0.0 | 0.0 | 0.0 |

Examples of Printed Polymeric Polyurethane Foam with Color Gamut Measurements
Sheet of Polymeric Polyurethane Foam Structure and Print Conditions A sheet of polymeric polyurethane foam obtained from the 3M Company's 3M Health Care business which is available commercially under the name Tegaderm Foam. The sheet of Tegaderm Foam was secured on a platen of a Konica Minolta XY200 inkjet printing system with a KM1024i print head with a printing gap (distance between nozzle plate and surface of the sheet of foam) set to 2 mm. The resolution was set at 360 dpi×360 dpi, wherein 360 dpi was the resolution in a machine direction and 360 dpi was the resolution in a cross direction. The print line velocity was 400 mm/s and the print head temperature was 45° C. The droplet size was set to 14 picoliters. The printed ink was cured with an off-line LED (light emitting diode) lamp at 53 feet/min having operating at 8 watts/cm² and a wavelength of 395 nm.

2500 color patches (6 mm by 6 mm individual color patches) were printed on a sheet of the Tegaderm Foam wherein the mean cell size of the Tegaderm Foam region was at least 100 microns but less than 500 microns. The printing was performed with Collins 186-150-6 LED Cyan Ink; Collins 186-150-7 LED Magenta Ink; Collins 186-150-6 LED Yellow Ink; and Collins 186-150-5 LED Black Ink.

The resulting color gamut was measured on the Tegaderm Foam according to the Color Gamut Test Method and defined by the CIELab coordinate values disposed inside the boundary described by the following system of equations:

$$\{a^*=-38.23 \text{ to } -32.61; b^*=17.17 \text{ to } -7.53\} \rightarrow b^*=-4.395a^*-150.852$$

$$\{a^*=-32.61 \text{ to } -25.35; b^*=-7.53 \text{ to } -27.38\} \rightarrow b^*=-2.734a^*-96.691$$

$$\{a^*=-25.35 \text{ to } -21.98; b^*=-27.38 \text{ to } -28.50\} \rightarrow b^*=-0.332a^*-35.805$$

$$\{a^*=-21.98 \text{ to } -12.95; b^*=-28.50 \text{ to } -29.14\} \rightarrow > b^*=-0.071a^*-30.058$$

$$\{a^*=-12.95 \text{ to } -3.87; b^*=-29.14 \text{ to } -27.66\} \rightarrow b^*=0.163a^*-27.029$$

$$\{a^*=-3.87 \text{ to } 0.44; b^*=-27.66 \text{ to } -25.08\} \rightarrow b^*=0.599a^*-25.343$$

$\{a^*=0.44 \text{ to } 18.96;\ b^*=-25.08 \text{ to } -16.12\} \rightarrow b^*=0.484a^*-25.293$ $\{a^*=18.96 \text{ to } 38.21;\ b^*=-16.12 \text{ to } -7.41\} \rightarrow b^*=0.452a^*-24.699$ $\{a^*=38.21 \text{ to } 33.25;\ b^*=-7.41 \text{ to } 25.54\} \rightarrow b^*=-6.643a^*+246.425$ $\{a^*=33.25 \text{ to } 27.34;\ b^*=25.54 \text{ to } 36.94\} \rightarrow b^*=-1.929a^*+89.677$ $\{a^*=27.34 \text{ to } -6.46;\ b^*=36.94 \text{ to } 59.02\} \rightarrow b^*=-0.653a^*+54.800$ $\{a^*=-6.46 \text{ to } -38.23;\ b^*=59.02 \text{ to } 17.17\} \rightarrow b^*=1.317a^*+67.530;$ and wherein L* is from 0 to 100.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A heterogeneous polymeric foam structure comprising:
a first surface and a second surface opposite the first surface;
interconnected open-cells obtained from at least one water-in-oil emulsion;
at least two distinct regions that differ by at least about 20% with regard to microcellular morphology; and
a graphic printed on at least one of the two distinct regions, wherein the graphic comprises ink positioned on the first surface; and
wherein a portion of the ink is positioned on the foam structure at an average ink penetration depth of 500 microns or less below the first surface.

2. The foam structure of claim 1, wherein graphic includes a primary color selected from the group consisting of: cyan, yellow, magenta, and black.

3. The foam structure of claim 2, wherein the primary color of cyan has an optical density of greater than about 0.10.

4. The foam structure of claim 2, wherein the primary color of yellow has an optical density of greater than about 0.10.

5. The foam structure of claim 2, wherein the primary color of magenta has an optical density of greater than about 0.10.

6. The foam structure of claim 2, wherein the primary color of black has an optical density of greater than about 0.10.

7. The foam structure of claim 1, wherein at least one of the distinct regions comprises a mean cell size of not more than about 50 μm.

8. The foam structure of claim 1, wherein at least one of the distinct regions comprises a mean cell size from about 20 μm to about 200 μm.

9. The foam structure of claim 1, wherein the at least two distinct regions comprises:
a first region comprising a mean cell size of not more than about 50 μm,
a second region comprising a mean cell size from about 20 μm to about 200 μm, wherein the mean cell size of the first region is less than the mean cell size of the second region.

10. A heterogeneous polymeric foam structure comprising:
a first surface and a second surface opposite the first surface;
interconnected open-cells obtained from at least one water-in-oil emulsion;
at least two distinct regions that differ by at least about 20% with regard to microcellular morphology; and
a graphic printed on at least one of the two distinct regions, the graphic comprising L*a*b* color values, the graphic being defined by the CIELab coordinate values disposed inside the boundary described by the following system of equations:

$\{a^*=2.35 \text{ to } -20.19;\ b^*=79.81 \text{ to } 70.46\} \rightarrow b^*=0.415a^*+78.835$ $\{a^*=-20.19 \text{ to } -40.21;\ b^*=70.46 \text{ to } 53.48\} \rightarrow b^*=0.848a^*+87.584$ $\{a^*=-40.21 \text{ to } -51.26;\ b^*=53.48 \text{ to } 20.56\} \rightarrow b^*=2.979a^*+173.273$ $\{a^*=-51.26 \text{ to } -53.16;\ b^*=20.56 \text{ to } 2.64\} \rightarrow b^*=9.432a^*+504.023$ $\{a^*=-53.16 \text{ to } -39.12;\ b^*=2.64 \text{ to } -30.65\} \rightarrow b^*=-2.371a^*-173.407$ $\{a^*=-39.12 \text{ to } -24.29;\ b^*=-30.65 \text{ to } -50.76\} \rightarrow b^*=-1.356a^*-83.698$ $\{a^*=-24.29 \text{ to } 5.66;\ b^*=-50.76 \text{ to } -44.78\} \rightarrow b^*=0.200a^*-45.910$ $\{a^*=5.66 \text{ to } 46.22;\ b^*=-44.78 \text{ to } -21.00\} \rightarrow b^*=0.586a^*-48.098$ $\{a^*=46.22 \text{ to } 52.70;\ b^*=-21.00 \text{ to } -12.76\} \rightarrow b^*=1.272a^*-79.774$ $\{a^*=52.70 \text{ to } 55.98;\ b^*=-12.76 \text{ to } 9.83\} \rightarrow b^*=6.887a^*-375.715$ $\{a^*=55.98 \text{ to } 43.71;\ b^*=9.83 \text{ to } 47.92\} \rightarrow b^*=-3.104a^*+183.610$ $\{a^*=43.71 \text{ to } 2.35;\ b^*=47.92 \text{ to } 79.81\} \rightarrow b^*=-0.771a^*+81.622;$ and wherein L* is from 0 to 100;
wherein the graphic comprises ink positioned on the first surface; and
wherein a portion of the ink is positioned on the foam structure at an average ink penetration depth of 500 microns or less below the first surface.

11. The foam structure of claim 10, wherein graphic includes a primary color selected from the group consisting of: cyan, yellow, magenta, and black.

12. The foam structure of claim 10, wherein graphic is positioned on a region comprising a mean cell size from about 20 μm to about 200 μm.

13. A heterogeneous polymeric foam structure comprising:
a first surface and a second surface opposite the first surface;
interconnected open-cells obtained from at least one water-in-oil emulsion;
at least two distinct regions that differ by at least about 20% with regard to microcellular morphology; and
a graphic printed on at least one of the two distinct regions, the graphic comprising L*a*b* color values, the graphic being defined by the CIELab coordinate values disposed inside the boundary described by the following system of equations:

$$\{a^* = -5.66 \text{ to } -13.27; b^* = 59.89 \text{ to } 57.29\} \to b^* = 0.342a^* + 61.824$$

$$\{a^* = -13.27 \text{ to } -25.02; b^* = 57.29 \text{ to } 40.39\} \to b^* = 1.438a^* + 76.376$$

$$\{a^* = -25.02 \text{ to } -35.25; b^* = 40.39 \text{ to } 14.23\} \to b^* = 2.557a^* + 104.371$$

$$\{a^* = -35.25 \text{ to } -35.55; b^* = 14.23 \text{ to } -0.42\} \to > b^* = 48.833a^* + 1735.605$$

$$\{a^* = -35.55 \text{ to } -16.05; b^* = -0.42 \text{ to } -40.40\} \to b^* = -2.050a^* - 73.307$$

$$\{a^* = -16.05 \text{ to } 5.30; b^* = -40.40 \text{ to } -32.69\} \to b^* = 0.361a^* - 34.604$$

$$\{a^* = 5.30 \text{ to } 34.81; b^* = -32.69 \text{ to } -12.63\} \to b^* = 0.680a^* - 36.293$$

$$\{a^* = 34.81 \text{ to } 39.33; b^* = -12.63 \text{ to } -5.99\} \to b^* = 1.469a^* - 63.767$$

$$\{a^* = 39.33 \text{ to } 44.16; b^* = -5.99 \text{ to } 17.53\} \to b^* = 4.870a^* - 197.510$$

$$\{a^* = 44.16 \text{ to } 42.52; b^* = 17.53 \text{ to } 33.24\} \to b^* = -9.579a^* + 440.550$$

$$\{a^* = 42.52 \text{ to } 0.92; b^* = 33.24 \text{ to } 58.23\} \to b^* = -0.601a^* + 58.783$$

$$\{a^* = 0.92 \text{ to } -5.66; b^* = 58.23 \text{ to } 59.89\} \to b^* = -0.252a^* + 58.462; \text{ and}$$

wherein L* is from 0 to 100,
wherein the graphic comprises ink positioned on the first surface; and
wherein a portion of the ink is positioned on the foam structure at an average ink penetration depth of 500 microns or less below the first surface.

14. The foam structure of claim 13, wherein graphic includes a primary color selected from the group consisting of: cyan, yellow, magenta, and black.

15. The foam structure of claim 13, wherein graphic is positioned on a region comprising a mean cell size of not more than about 50 μm.

16. A heterogeneous polymeric foam structure comprising:
interconnected open-cells obtained from at least one water-in-oil emulsion;
at least two distinct regions that differ by at least about 20% with regard to microcellular morphology;
a first surface;
a second surface opposite the first surface;
a graphic printed directly on the first surface, wherein the graphic comprises ink positioned on the first surface, and wherein a portion of the ink is positioned at an average ink penetration depth of 500 microns or less below the first surface; and
wherein foam structure has a dry average ink adhesion rating of at least about 1.5 or greater.

17. The foam structure of claim 16, wherein graphic includes a primary color selected from the group consisting of: cyan, yellow, magenta, and black, wherein at least one primary color has an optical density of greater than about 0.10.

18. The foam structure of claim 16, wherein at least one of the distinct regions comprises a mean cell size of not more than about 50 μm.

19. The foam structure of claim 16, wherein at least one of the distinct regions comprises a mean cell size from about 20 μm to about 200 μm.

20. The foam structure of claim 16, wherein the at least two distinct regions comprises:
a first region comprising a mean cell size of not more than about 50 μm,
a second region comprising a mean cell size from about 20 μm to about 200 μm.

21. A heterogeneous polymeric foam structure comprising:
interconnected open-cells obtained from at least one water-in-oil emulsion;
at least two distinct regions that differ by at least about 20% with regard to microcellular morphology;
a first surface;
a second surface opposite the first surface;
a graphic printed directly on the first surface, wherein the graphic comprises ink positioned on the first surface, and wherein a portion of the ink is positioned on the foam structure at an average ink penetration depth of 500 microns or less below the first surface; and
wherein foam structure has a wet average ink adhesion rating of at least about 1.5 or greater.

22. The foam structure of claim 21, wherein graphic includes a primary color selected from the group consisting of: cyan, yellow, magenta, and black, wherein at least one primary color has an optical density of greater than about 0.10.

23. The foam structure of claim 21, wherein at least one of the distinct regions comprises a mean cell size of not more than about 50 μm.

24. The foam structure of claim 21, wherein at least one of the distinct regions comprises a mean cell size from about 20 μm to about 200 μm.

25. The foam structure of claim 21, wherein the at least two distinct regions comprises:
a first region comprising a mean cell size of not more than about 50 μm,
a second region comprising a mean cell size from about 20 μm to about 200 μm.

26. A polymeric foam structure comprising:
   interconnected open-cells obtained from at least one water-in-oil emulsion;
   a first surface;
   a second surface opposite the first surface; and
   a graphic printed on the first surface; and
   wherein the graphic comprises ink positioned on the first surface, and wherein a portion of the ink is positioned on the foam structure at an average ink penetration depth of 500 microns or less below the first surface.

27. The foam structure of claim 26, wherein graphic includes a primary color selected from the group consisting of: cyan, yellow, magenta, and black.

28. The foam structure of claim 27, wherein the primary color of cyan has an optical density of greater than about 0.10.

29. The foam structure of claim 27, wherein the primary color of yellow has an optical density of greater than about 0.10.

30. The foam structure of claim 27, wherein the primary color of magenta has an optical density of greater than about 0.10.

31. The foam structure of claim 27, wherein the primary color of black has an optical density of greater than about 0.10.

32. The foam structure of claim 26, wherein the first surface comprises a region comprising a mean cell size of not more than about 50 μm.

33. The foam structure of claim 26, wherein the first surface comprises a region comprising a mean cell size from about 20 μm to about 200 μm.

34. A polymeric foam structure comprising:
   interconnected open-cells obtained from at least one water-in-oil emulsion;
   a first surface and a second surface opposite the first surface; and
   a graphic printed on the first surface, the graphic comprising L*a*b* color values, the graphic being defined by the CIELab coordinate values disposed inside the boundary described by the following system of equations:

$$\{a^*=2.35 \text{ to } -20.19; b^*=79.81 \text{ to } 70.46\} \rightarrow b^*=0.415a^*+78.835$$

$$\{a^*=-20.19 \text{ to } -40.21; b^*=70.46 \text{ to } 53.48\} \rightarrow b^*=0.848a^*+87.584$$

$$\{a^*=-40.21 \text{ to } -51.26; b^*=53.48 \text{ to } 20.56\} \rightarrow b^*=2.979a^*+173.273$$

$$\{a^*=-51.26 \text{ to } -53.16; b^*=20.56 \text{ to } 2.64\} \rightarrow > b^*=9.432a^*+504.023$$

$$\{a^*=-53.16 \text{ to } -39.12; b^*=2.64 \text{ to } -30.65\} \rightarrow b^*=-2.371a^*-173.407$$

$$\{a^*=-39.12 \text{ to } -24.29; b^*=-30.65 \text{ to } -50.76\} \rightarrow b^*=-1.356a^*-83.698$$

$$\{a^*=-24.29 \text{ to } 5.66; b^*=-50.76 \text{ to } -44.78\} \rightarrow b^*=0.200a^*-45.910$$

$$\{a^*=5.66 \text{ to } 46.22; b^*=-44.78 \text{ to } -21.00\} \rightarrow b^*=0.586a^*-48.098$$

$$\{a^*=46.22 \text{ to } 52.70; b^*=-21.00 \text{ to } -12.76\} \rightarrow b^*=1.272a^*-79.774$$

$$\{a^*=52.70 \text{ to } 55.98; b^*=-12.76 \text{ to } 9.83\} \rightarrow b^*=6.887a^*-375.715$$

$$\{a^*=55.98 \text{ to } 43.71; b^*=9.83 \text{ to } 47.92\} \rightarrow b^*=-3.104a^*+183.610$$

$$\{a^*=43.71 \text{ to } 2.35; b^*=47.92 \text{ to } 79.81\} \rightarrow b^*=-0.771a^*+81.622; \text{ and}$$

wherein L* is from 0 to 100; and
   wherein the graphic comprises ink positioned on the first surface, and wherein a portion of the ink is positioned on the foam structure at an average ink penetration depth of 500 microns or less below the first surface.

35. The foam structure of claim 34, wherein graphic includes a primary color selected from the group consisting of: cyan, yellow, magenta, and black.

36. The foam structure of claim 34, wherein graphic is positioned on a region comprising a mean cell size from about 20 μm to about 200 μm.

37. A polymeric foam structure comprising:
   interconnected open-cells obtained from at least one water-in-oil emulsion;
   a first surface and a second surface opposite the first surface; and
   a graphic printed on the first surface, the graphic comprising L*a*b* color values, the graphic being defined by the CIELab coordinate values disposed inside the boundary described by the following system of equations:

$$\{a^*=-5.66 \text{ to } -13.27; b^*=59.89 \text{ to } 57.29\} \rightarrow b^*=0.342a^*+61.824$$

$$\{a^*=-13.27 \text{ to } -25.02; b^*=57.29 \text{ to } 40.39\} \rightarrow b^*=1.438a^*+76.376$$

$$\{a^*=-25.02 \text{ to } -35.25; b^*=40.39 \text{ to } 14.23\} \rightarrow b^*=2.557a^*+104.371$$

$$\{a^*=-35.25 \text{ to } -35.55; b^*=14.23 \text{ to } -0.42\} \rightarrow > b^*=48.833a^*+1735.605$$

$$\{a^*=-35.55 \text{ to } -16.05; b^*=-0.42 \text{ to } -40.40\} \rightarrow b^*=-2.050a^*-73.307$$

$$\{a^*=-16.05 \text{ to } 5.30; b^*=-40.40 \text{ to } -32.69\} \rightarrow b^*=0.361a^*-34.604$$

$$\{a^*=5.30 \text{ to } 34.81; b^*=-32.69 \text{ to } -12.63 \rightarrow b^*=0.680a^*-36.293$$

$$\{a^*=34.81 \text{ to } 39.33; b^*=-12.63 \text{ to } -5.99\} \rightarrow b^*=1.469a^*-63.767$$

$$\{a^*=39.33 \text{ to } 44.16; b^*=-5.99 \text{ to } 17.53\} \rightarrow b^*=4.870a^*-197.510$$

$$\{a^*=44.16 \text{ to } 42.52; b^*=17.53 \text{ to } 33.24\} \rightarrow b^*=-9.579a^*+440.550$$

$$\{a^*=42.52 \text{ to } 0.92; b^*=33.24 \text{ to } 58.23\} \rightarrow b^*=-0.601a^*+58.783$$

$$\{a^*=0.92 \text{ to } -5.66; b^*=58.23 \text{ to } 59.89\} \rightarrow b^*=-0.252a^*+58.462; \text{ and}$$

wherein L* is from 0 to 100; and
   wherein the graphic comprises ink positioned on the first surface, and wherein a portion of the ink is positioned on the foam structure at an average ink penetration depth of 500 microns or less below the first surface.

38. The foam structure of claim 37, wherein graphic includes a primary color selected from the group consisting of: cyan, yellow, magenta, and black.

39. The foam structure of claim 37, wherein graphic is positioned on a region comprising a mean cell size of not more than about 50 µm.

40. A polymeric foam structure comprising:
- interconnected open-cells obtained from at least one water-in-oil emulsion;
- a first surface;
- a second surface opposite the first surface;
- a graphic printed directly on the first surface, and
- wherein foam structure has a dry average ink adhesion rating of at least about 1.5 or greater.

41. The foam structure of claim 40, wherein the graphic comprises ink positioned on the first surface.

42. The foam structure of claim 41, wherein a portion of the ink is positioned at an average ink penetration depth of 500 microns or less below the first surface.

43. The foam structure of claim 40, wherein graphic includes a primary color selected from the group consisting of: cyan, yellow, magenta, and black, wherein at least one primary color has an optical density of greater than about 0.10.

44. The foam structure of claim 40, wherein the first surface comprises a region comprising a mean cell size of not more than about 50 µm.

45. The foam structure of claim 40, wherein the first surface comprises a region comprising a mean cell size from about 20 µm to about 200 µm.

46. A polymeric foam structure comprising:
- interconnected open-cells obtained from at least one water-in-oil emulsion;
- a first surface;
- a second surface opposite the first surface;
- a graphic printed directly on the first surface, wherein the graphic comprises ink positioned on the first surface, and wherein a portion of the ink is positioned on the foam structure at an average ink penetration depth of 500 microns or less below the first surface; and
- wherein foam structure has a wet average ink adhesion rating of at least about 1.5 or greater.

47. The foam structure of claim 46, wherein graphic includes a primary color selected from the group consisting of: cyan, yellow, magenta, and black, wherein at least one primary color has an optical density of greater than about 0.10.

48. The foam structure of claim 46, wherein the first surface comprises a region comprising a mean cell size of not more than about 50 µm.

49. The foam structure of claim 46, wherein the first surface comprises a region comprising a mean cell size from about 20 µm to about 200 µm.

50. A polyurethane foam structure comprising:
- interconnected open-cells obtained from a reaction product of at least one polyol component and a diisocyanate component;
- a first surface;
- a second surface opposite the first surface; and
- a graphic printed on the first surface; and
- wherein the graphic comprises ink positioned on the first surface, and wherein a portion of the ink is positioned on the foam structure at an average ink penetration depth of 500 microns or less below the first surface.

51. The polyurethane foam structure of claim 50, wherein graphic includes a primary color selected from the group consisting of: cyan, yellow, magenta, and black.

52. The polyurethane foam structure of claim 51, wherein the primary color of cyan has an optical density of greater than about 0.10.

53. The polyurethane foam structure of claim 51, wherein the primary color of yellow has an optical density of greater than about 0.10.

54. The polyurethane foam structure of claim 51, wherein the primary color of magenta has an optical density of greater than about 0.10.

55. The polyurethane foam structure of claim 51, wherein the primary color of black has an optical density of greater than about 0.10.

56. A hydrophilic, flexible, nonionic polymeric foam structure comprising:
- interconnected open-cells;
- a first surface;
- a second surface opposite the first surface; and
- a graphic printed on the first surface; and
- wherein the graphic comprises ink positioned on the first surface, and wherein a portion of the ink is positioned on the foam structure at an average ink penetration depth of 500 microns or less below the first surface.

* * * * *